(12) United States Patent
Dafni

(10) Patent No.: US 8,537,965 B2
(45) Date of Patent: Sep. 17, 2013

(54) CONE-BEAM CT

(75) Inventor: Ehud Dafni, Caesarea (IL)

(73) Assignee: Arineta Ltd., Caesarea (IL)

( * ) Notice: Subject to any disclaimer, the term of this patent is extended or adjusted under 35 U.S.C. 154(b) by 211 days.

(21) Appl. No.: 12/965,968

(22) Filed: Dec. 13, 2010

(65) Prior Publication Data
US 2011/0080992 A1    Apr. 7, 2011

Related U.S. Application Data

(63) Continuation-in-part of application No. 12/307,374, filed as application No. PCT/IL2007/000462 on Apr. 10, 2007, now Pat. No. 7,869,561.

(51) Int. Cl.
*G01N 23/00* (2006.01)

(52) U.S. Cl.
USPC .................................. 378/9; 378/4

(58) Field of Classification Search
USPC .......................................... 378/9, 4
See application file for complete search history.

(56) References Cited

U.S. PATENT DOCUMENTS

| | | | |
|---|---|---|---|
| 4,637,040 A | 1/1987 | Sohval et al. | |
| 4,689,809 A | 8/1987 | Sohval | |
| 4,912,739 A | 3/1990 | Weiss | |
| 5,068,882 A | 11/1991 | Eberhard | |
| 5,125,012 A | 6/1992 | Schittenhelm | |
| 5,187,659 A | 2/1993 | Eberhard et al. | |
| 5,625,661 A | 4/1997 | Oikawa | |
| 5,712,889 A | 1/1998 | Lanzara et al. | |
| 5,966,422 A | 10/1999 | Dafni et al. | |
| 6,125,167 A | 9/2000 | Morgan | |
| 6,181,771 B1 | 1/2001 | Hell et al. | |
| 6,229,870 B1 | 5/2001 | Morgan | |
| 6,233,309 B1 | 5/2001 | Baptist | |
| 6,483,890 B1 | 11/2002 | Malamud | |
| 6,996,204 B2 | 2/2006 | Grass et al. | |
| 7,016,455 B2 | 3/2006 | Bruder et al. | |

(Continued)

FOREIGN PATENT DOCUMENTS

| | | |
|---|---|---|
| EP | 1028451 | 8/2000 |
| EP | 1570785 | 9/2005 |

(Continued)

OTHER PUBLICATIONS

Communication Pursuant to Article 94(3) EPC Dated May 27, 2010 From the Euroepan Patent Office Re. Application No. 07736206.8.

(Continued)

*Primary Examiner* — Hoon Song

(57) ABSTRACT

An X-ray source system for a CT scanner includes a plurality of X-ray sources, wherein each X-ray source of the plurality is provided with a cathode from which an electron beam is emitted, an anode to receive the electron beam and at least one grid electrode, wherein the grid electrodes are configured to selectably block radiation from said X-ray sources; a high voltage generator for applying voltage to the plurality of X-ray sources, wherein each of the plurality of X-ray sources are configured to present substantially the same load to the high voltage generator; a grid modulator configured to apply voltage to grid electrodes of each of the plurality of X-ray sources in turn; and a controller for controlling the grid modulator so that only one of the plurality of X-ray sources emits radiation at any one time.

28 Claims, 15 Drawing Sheets

(56) References Cited

U.S. PATENT DOCUMENTS

| | | | |
|---|---|---|---|
| 7,039,152 | B2 | 5/2006 | Bruder et al. |
| 7,039,153 | B2 | 5/2006 | Bruder et al. |
| 7,072,436 | B2 | 7/2006 | Pelc |
| 7,145,981 | B2 | 12/2006 | Pelc |
| 7,792,241 | B2 | 9/2010 | Wu et al. |
| 2003/0108146 | A1 | 6/2003 | Malamud |
| 2005/0135550 | A1 | 6/2005 | Man et al. |
| 2005/0195935 | A1* | 9/2005 | Yahata ............... 378/4 |
| 2006/0023833 | A1 | 2/2006 | Seufert |
| 2006/0233297 | A1* | 10/2006 | Ishiyama ............ 378/9 |
| 2006/0285633 | A1 | 12/2006 | Sukovic et al. |
| 2010/0020935 | A1 | 1/2010 | Dafni |
| 2010/0080357 | A1 | 4/2010 | Katcha et al. |
| 2010/0104062 | A1 | 4/2010 | Wu et al. |

FOREIGN PATENT DOCUMENTS

| | | |
|---|---|---|
| JP | 2004-154276 | 6/2003 |
| WO | WO 2006/038145 | 4/2006 |
| WO | WO 2006/090323 | 8/2006 |
| WO | WO 2008/122970 | 10/2008 |
| WO | WO 2008/122971 | 10/2008 |

OTHER PUBLICATIONS

Communication Relating to the Results of the Partial International Search Dated Dec. 21, 2007 From the International Searching Authority Re.: Application No. PCT/IL2007/000461.

International Preliminary Report on Patentability Dated Oct. 22, 2009 From the International Bureau of WIPO Re.: Application No. PCT/IL2007/000461.

International Preliminary Report on Patentability Dated Oct. 22, 2009 From the International Bureau of WIPO Re.: Application No. PCT/IL2007/000462.

International Search Report and the Written Opinion Dated Dec. 19, 2007 From the International Searching Authority Re.: Application No. PCT/IL2007/000462.

International Search Report and the Written Opinion Dated Mar. 20, 2008 From the International Searching Authority Re.: Application No. PCT/IL2007/00461.

Office Action Dated Oct. 4, 2010 From the Israel Patent Office Re. Application No. 196359 and Its Translation Into English.

Response Dated Sep. 5, 2010 to Communication Pursuant to Article 94(3) EPC of May 27, 2010 From the Euroepan Patent Office Re. Application No. 07736206.8.

Feldkamp et al. "Practical Cone-Beam Algorithm", Journal of the Optical Society America A, 1(6): 612-619, Jun. 1984.

Tuy "An Inversion Formula for Cone-Beam Reconstruction", Society for Industrial and Applied Mathematics, SIAM Journal on Applied Mathematics, 43(3): 546-552, Jun. 1983.

Response Dated Feb. 2, 2011 to Office Action of Oct. 4, 2010 From the Israel Patent Office Re. Application No. 196359.

Office Action Dated Mar. 13, 2011 From the Israel Patent Office Re. Application No. 196359 and Its Translation Into English.

Response Dated Mar. 24, 2011 to Official Action of Mar. 7, 2011 From the US Patent and Trademark Office Re. U.S. Appl. No. 12/574,795.

Communication Under Rule 71(3) EPC Dated Aug. 28, 2012 From the European Patent Office Re. Application No. 07736206.8.

Official Action Dated May 11, 2011 From the US Patent and Trademark Office Re. U.S. Appl. No. 12/574,795.

Official Action Dated Mar. 7, 2011 From the US Patent and Trademark Office Re. U.S. Appl. No. 12/574,795.

Official Action Dated Jun. 24, 2013 From the US Patent and Trademark Office Re. U.S. Appl. No. 12/574,795.

* cited by examiner

CONE-BEAM CT

RELATED APPLICATIONS

This application is continuation-in-part (CIP) of U.S. patent application Ser. No. 12/307,374 filed on Jan. 5, 2009, which is a National Phase of PCT Patent Application No. PCT/IL2007/000462 filed on Apr. 10, 2007. The contents of the above applications are incorporated herein by reference in their entirety.

FIELD OF THE INVENTION

The invention relates to computerized tomography (CT) systems. Some embodiments relate to multiple source cone-beam CT for rapid scanning.

BACKGROUND OF THE INVENTION

Many conventional CT scanner utilize X-ray radiation beams formed as one or more narrow fans, where each fan, with its corresponding line of detectors, defines a slice in the subject. The scan is performed either slice-by-slice by moving the subject along the scanner rotation axis and stopping it while a radial scan is taken, or a helical scan is performed where the subject moves simultaneously with the scanning.

Multi-slice scanning as described above with currently available scanners reaches a width in the order of 40 mm. Thus, to scan a typical organ requires translating the subject axially along the rotation axis. When moving organs are involved, however, especially the beating heart, the temporal resolution, i.e. 'freezing' the organ, is problematic. Various techniques were developed to tackle the problem such as gating by ECG or learning the rhythm, with varying degrees of success.

One area of current interest is CT scanning of the heart, referred to as "cardiac CT." This presents especially difficult problems since the length of image that is required is of the order of 120 mm. Furthermore, for best results it is desirable to acquire all of the data in a one half plus fan beam angle rotation or in a single rotation. A half plus rotation can be made in 180 milliseconds, which, for proper phase within the diastole would result in sufficiently consistent data for reconstruction.

To overcome the limited width and reduce the numerous rotations of radiation/detector around the subject, some approaches were suggested where a multiplicity of radiation sources are used with linear or two-dimensional detectors. For example, U.S. Pat. Nos. 5,966,422, 7,016,455, 7,039,152 and 7,039,153 describe CT systems utilizing multiple fan beams sources arranged circumferentially about the CT rotation axis, each with a corresponding detector array. The disclosures of these references are incorporated herein by reference.

U.S. Pat. No. 5,625,661, the disclosure of which is incorporated by reference, describes a system in which a plurality of axially displaced sources of X-rays are used to irradiate the patient. This system has a number of rows of detectors equal to the number of sources. Since the number of sources would be limited and a required resolution would indicate a detector width of at most 2 mm, the system has a limited patient coverage and is described only in a spiral scan mode. Thus, this system does not allow for single or half rotation cardiac CT scanning.

U.S. Pat. Nos. 5,712,889 and 6,229,870, the disclosures of which are incorporated by reference, describe X-ray sources and systems in which plurality of axially displaced sources emit a plurality of parallel fan beams, formed by array of septa, each irradiating different parts of the scanned subject and directed at different part of the detector array. These systems are inherently inefficient in utilization of the X radiation since most radiation is absorbed by the septa while still requiring high power, generating high heat load, to energize the sources.

Cone-beam scanning is also known where a cone of radiation covers a substantial section of the subject. In cone beam scanning an X-ray source irradiates the subject over a relatively larger solid angle and an opposing area detector on the other side of the subject detects the transmitted radiation. Thus, a wide cone beam system covers a much larger portion of the subject relative to a fan beam or a narrow cone beam. With the larger area coverage, translating the subject is avoided or more limited, and a fast scanning is possible with, in principle, better temporal resolution.

The simplest cone beam scan mode is a rotation of a single source (and detector array) about the subject (circular source trajectory), although a partial scan (less than 360°) is also possible.

The reconstruction algorithm used for reconstructing cone beam acquired data is usually of the type called "Feldkamp" or "FDK" method (Feldkamp, L. A., L. Davis, and J. Kress (1984). *Practical Cone-beam Algorithm. Journal of the Optical Society of America* 1, 612-619, the disclosure of which is incorporated herein by reference) or a derivative thereof. The FDK algorithm is approximate and allows the scanned subject to extend outside the projected region in the axial direction. Unfortunately, with these types of solutions the reconstructed images have artifacts that worsen with the distance from the mid plane (the source trajectory plane) due to "data incompleteness". Similar problems occur with other reconstruction algorithms known in the art.

It is usually accepted that data completeness leading to exact reconstruction is available if the Tuy-Smith condition is met (Tuy, H. (1983). *An inversion formula for cone-beam reconstruction. SIAM Journal of Applied Mathematics* 43, 546-552, the disclosure of which is incorporated herein by reference). This condition requires that the source trajectory shall intersect every plane passing through the scanned subject volume of interest. This is definitely not the case for a cone beam single circular source trajectory.

FIG. 1 shows a simplified schematic axial cross-sectional presentation of the use of a single cone beam to irradiate a patient. The use of very large cone angles, sufficient to encompass the heart have been mooted and are under development. However, as can be understood from the following discussion, they are expensive and unnecessarily irradiate the patient.

FIG. 1 shows a single cone beam system 10 of the prior art having a single source 12 and a detector array 14. It should be understood that each detector element 16 shown in FIG. 1 corresponds to a linear circumferential or planar linear array of detector elements. In a typical geometry each detector elements covers 0.5 mm width at an axis of rotation 58. Reference 18 represents a cylinder of reconstruction (patient). Cone beam 20 is seen to intersect patient 18 in three distinct regions. A first region 22 is a region in which data can be acquired over all rotation angles and is referred to herein as the region of full coverage. A second region 24 on each side of region 22 corresponds to regions of data acquisition, in which data is available over all rotation angles only at diameters smaller than the scanned subject diameter. Region 26 on either side of region 24 corresponds to volume irradiated only at particular gantry angles, in which data is not available for a half or a whole rotation. Since the region of full coverage is so much smaller than the spread of the beam at the detector for imaging the heart in a single rotation, the number of detector rows must be increased from typically 240 rows to cover the heart to about 280 rows. Further, larger parts of the patient are subject to ionizing radiation than should optimally be irradiated. With the geometry of FIG. 1, even in region 24 the data does not meet the Tuy-Smith condition, except for data close the focal spot rotation plan, resulting in degraded image quality for parts of the subject away from the rotation plan.

U.S. Pat. No. 6,996,204, the disclosure of which is incorporated herein by reference describe a method in which a cone beam scanner with geometry similar to that described in FIG. 1 is used in steps: cone beam attenuation data is acquired for one circular trajectory of the source, the scanned subject is axially translated relative to the source, cone beam data is acquired again for a second circular trajectory of the source such that the two cone beams have a volume of overlap and images are reconstructed where for volume elements in the volume of overlap data is used from both source trajectories. The method disclosed reduces the amount of missing data and improves the resulted image quality. However, the method cannot be used for a single heart beat cardiac scanning since it involves two acquisition cycles separated in time.

U.S. Pat. Nos. 5,068,882 and 5,187,659, the disclosures of which are incorporated herein by reference describe systems wherein two overlapping cone beam sources are provided and data is acquired from both within a single rotation of the sources relative to the scanned subject. In the disclosed embodiments, the sources are displaced both axially and radially and each is provided with a two dimensional detector array, thus increasing cost and complexity of the systems.

U.S. Pat. Nos. 7,072,436 and 7,145,981 describe systems in which two dimensional arrays of radiation sources are provided with extent in both axial and angular directions. A common detector array is provided to receive attenuated radiation from said sources.

The use of X-ray beams in medical imaging is well established. X-ray projection imaging is used to obtain static or fluoroscopic images. Computerized tomography (CT) scanning uses a plurality of X-ray images to assemble a 3D reconstruction of an organ or a potion of a subject. In both cases, single focal spots are typically used. However, there are imaging systems using multiple focal spots.

U.S. Pat. No. 6,181,771 to Hell describes electro magnetic deflection of an electron beam emanating from a cathode in an X-ray tube using a pair of electro-magnets placed on opposite sides of the beam. Hell is concerned primarily with focusing the electron beam at a focal spot on an anode. The disclosure of this patent is fully incorporated herein by reference.

U.S. Pat. No. 6,483,890 to Malamud, describes an X-ray tube with a single cathode and a single anode. The X-ray tubes described by Malamud includes four deflection plates arranged in pairs. Malamud describes using a changing voltage applied between each pair to cause an electron beam to rotate in a circle about its nominal axial path through a midpoint between the four deflection plates. Malamud is concerned primarily with focusing the beam at different places on the anode using a predetermined temporal pattern. The disclosure of this patent is fully incorporated herein by reference.

U.S. Pat. No. 4,689,809 to Sohval describes an X-ray tube with a similar physical configuration to that of Malamud and/or Hell. Sohval, like Malamud and Hell uses an electromagnetic field to deflect a beam of electrons originating from a cathode in an X-ray tube. The disclosure of this patent is fully incorporated herein by reference. U.S. Pat. No. 4,637,040 describes a CT system utilizing this X-ray tube.

U.S. Pat. No. 4,912,739 to Weiss also describes use of an electromagnetic field to deflect a beam of electrons originating from a cathode in an X-ray tube. The disclosure of this patent is fully incorporated herein by reference.

U.S. Pat. No. 6,229,870 to Morgan describes a plurality of discrete anodes mounted within the vacuum envelope, the anodes selectively generating a plurality of parallel X-ray beams. According to Morgan, each anode element is associated with a cathode assembly selectably excitable by a filament power supply. When selected, each cathode assembly generates an electron stream which strikes the corresponding anode element and produces X-ray beams. The disclosure of this patent is fully incorporated herein by reference.

Grid control and Grid pulsing for X-ray tubes is well known and has been commercialized, for example in the MRC line of X-ray tubes of Phillips Medical Systems.

US Patent Publication No. 2006/0285633 to Sukovic, the contents of which are incorporated by reference herein, describes a multi-source CT scanner with a plurality of cone-beam X-ray sources offset along a CT axis. The CT scanner includes a controller programmed to alternately activate a first and second X-ray source. It is further stated that although the X-ray sources in both embodiments described are shown as completely separate, a single, multiple-source unit could also be utilized where a power supply or other circuitry are shared between the multiple sources.

US Patent Publication No. 2005/0195935 to Yahata, the contents of which is incorporated by reference herein, describes an X-ray generator that generates two cone beam X-radiations which pass through two successive slabs. It is described that an X-ray tube permitting alternate X-irradiations includes a double set of an anode, a cathode, a grid and a switch. One of a 0 bias voltage and a negative bias voltage is applied to each of the grids via the switch. The negative voltage assumes a value permitting blocking of an electron flow between a cathode and an anode. Consequently, X-irradiation can be discontinued by changing the connections to be made via the switches. The connections to be made via the switch are changed with either of signals that are out of phase with each other. It is mentioned that since the X-ray tube has two grids associated with the two pairs of an anode and a cathode, the timings of generating two cone beam X-radiations can be controlled.

SUMMARY OF THE INVENTION

An general aspect of some embodiments of the invention relate to an apparatus for CT cone beam scanning comprising a plurality of radiation cone beam sources spaced in a direction parallel to the rotation axis.

An aspect of some embodiments of the present invention provides for an X-ray source system for a CT scanner comprising: a plurality of X-ray sources, wherein each X-ray source of the plurality is provided with a cathode from which an electron beam is emitted, an anode to receive the electron beam and at least one grid electrode, wherein the grid electrodes are configured to selectably block radiation from said X-ray sources; a high voltage generator for applying voltage to the plurality of X-ray sources, wherein each of the plurality of X-ray sources are configured to present substantially the same load to the high voltage generator; a grid modulator configured to apply voltage to grid electrodes of each of the plurality of X-ray sources in turn; and a controller for controlling the grid modulator so that only one of the plurality of X-ray sources emits radiation at any one time.

Optionally, the grid modulator is configured to alternately provide a pulsed voltage to at least one of the plurality of X-ray sources for blocking the radiation, the pulsed voltage pulsed at a frequency between 0.5 KHz to 10 KHz.

Optionally, the grid modulator is configured to provide a pulsed voltage for blocking the radiation with a duty cycle of 50% or more.

Optionally, the high voltage generator supplies a continuous voltage during switching between each of the plurality of X-ray sources.

Optionally, the grid modulator is configured to apply a same voltage to a plurality of grid electrodes associated with any one of the plurality of X-ray sources.

Optionally, the grid modulator is configured to apply a different voltage to each of a plurality of grid electrodes associated with any one of the plurality of X-ray sources.

Optionally, the grid modulator applies voltages between 0 and −5 KV to the grid electrodes.

Optionally, the high voltage generator generates voltages between 80 KV to 140 KV.

Optionally, the plurality of X-ray sources includes two X-ray tubes.

Optionally, the grid modulator is additionally configured for modulating the grid voltages for focal spot position modulation.

Optionally, at least one pair of grid electrodes are configured to focus the electron beam to reduce a size of a focal spot on an anode.

Optionally, voltages are applied to the at least one grid electrode of a X-ray source over a period of time, and wherein the grid modulator is configured to apply voltages for blocking radiation from the X-ray source during one part of the period and to apply voltages for steering or focusing the electron beam of the X-ray source during another part of the period.

Optionally, the voltages applied to the at least one grid electrode are pulsed voltages.

Optionally, the plurality of X-ray sources are cone beam sources.

An aspect of some embodiments of the present invention provides for an apparatus for CT cone beam scanning, comprising: a table for holding a subject; a gantry; a first detector array, mounted on the gantry; an X-ray source system as described herein above; and a scanning controller that acquires data responsive to radiation from the plurality of X-ray sources from the detector array attenuated by at least part of a common volume of a subject irradiated by the plurality of X-ray sources.

Optionally, the apparatus includes a collimator that collimates the cone beams such that the cone beams from two of said at least two sources are asymmetrical with respect to a plane defined by each respective source trajectory about the rotation axis and the edge of at least one asymmetrical cone beam which is farther from the other source makes a larger angle to the detector array than does the beam edge closer to the other source; and such that the farther edge of the at least one cone beam makes an angle of between 87 and 90 degrees with the detector array.

Optionally, the detector array has a given number of rows of detector elements spaced along a rotation axis of the gantry.

Optionally, the number of rows is at least twice the number of sources.

Optionally, the apparatus includes a second detector array, having a given number of rows of detector elements spaced along an rotation axis of the gantry, mounted on the gantry; a second plurality of X-ray sources mounted on the gantry for rotation about the patient table on the rotation axis, the number of rows being at least twice the number of sources; and wherein the scanning controller acquires data responsive to radiation from the first and second plurality of sources from both the first and second detector arrays attenuated by at least part of the common volume of the subject irradiated by the first and second plurality of radiation sources.

Optionally, the second detector array and the second plurality of X-ray sources are circumferentially offset from the first detector array and first plurality of X-ray sources.

An aspect of some embodiments of the present invention provides for a method for activating a plurality of X-ray sources for CT scanning, the method comprising: providing a plurality of X-ray sources each including at least one grid electrode; applying voltage to each of the plurality of X-ray sources with a single high voltage generator; and enabling radiation from one of the plurality of X-sources at a time and blocking radiation from said other X-ray sources of the plurality with the grid of electrodes so that only one of the plurality of X-ray sources emits radiation at any one time; wherein each of the plurality of X-ray sources apply substantially the same load to the high voltage generator.

Optionally, the voltage applied to said grid electrodes is a pulsed voltage that is pulsed at a frequency between 0.5 KHz to 10 KHz.

Optionally, the pulse voltage has a duty cycle of 50% or more.

Optionally, the high voltage applied to said plurality of X-ray sources by said HV generator is a continuous voltage.

Optionally, a same voltage is applied to each of the grid electrodes associated with any one of the plurality of X-ray sources.

Optionally, the grid voltage applied to said grid electrodes is between 0 and −5 KV.

Optionally, the high voltage generator generates voltages between 80 KV to 140 KV.

Optionally, the plurality of X-ray sources includes two X-ray tubes.

Optionally, the plurality of X-ray sources includes a plurality of X-ray sources in a single vacuum enclosure.

According to an aspect of some embodiments of the invention, the irradiation that passes through the patient utilizes at least part of a common detector array. In some embodiments of the invention, data from radiation generated by multiple beams is captured substantially over the same area of a common detector array. In exemplary embodiments of the invention only two sources are used. In exemplary embodiments of the invention the number of detector rows is larger, optionally by a factor of two or more, than the number of sources. Optionally, the number of rows of detectors is not a multiple of the number of sources and can be as high as 10 or 100 or 1000 times as large as the number of sources.

An aspect of some embodiments of the invention is concerned with the acquisition of a complete set of CT data sufficient for the reconstruction of the human heart in a 180 degree angle rotation (plus an additional angle, but substantially less than a full rotation) of the sources about the patient. In an embodiment of the invention, this data is generated substantially without irradiating the patient with substantial radiation not used in the reconstruction. Substantial radiation not used in the reconstruction is defined here as a situation where over 10% or 20% of the irradiated axis is not in the region of full coverage as defined above. Adding an additional angle for half rotation acquisition in cone beam is well known. It is estimated that in the present invention, an additional 20 to 40 degrees is added, although a lesser amount could be added.

In some exemplary embodiments of the invention, the radiation sources are housed in a single vacuum housing. In some exemplary embodiments of the invention, the radiation sources are in separate vacuum volumes.

In some exemplary embodiments of the invention, each source is energized and generates radiation in sequence. In some embodiments the frequency with which the sources are energized is high enough so that data is acquired from both sources at substantially the same circumferential position. In some embodiments, the data is corrected to take into account the small differences in rotation position of radiation from the two sources.

In some embodiments the switching is periodic at a frequency high enough to provide sufficient number of views for each source and data from successive energizing is interpolated to be matched with data from the other source. A method for combining such data is taught in Th. Köhler, R. Proksa and M. Grass, "A fast and efficient method for sequential cone-beam tomography", Medical Physics November 2001 Volume 28, Issue 11, pp. 2318-2327.

Rotation time in cardiac scanners would be in the range 200-400 msec per rotation. Lets assume it is 250 msec. A minimum of 500 views per rotation is needed but 750 views/rotation for each source would be a better choice. The switching frequency to get 750 views×2 sources would be 3 KHz (0.333 msec cycle, each source is 0.176 msec on and 0.167 msec off).

In other embodiments the sources are energized closely spaced in time and then are energized again after the source has rotated by a small angle.

In exemplary embodiments of the invention, the plurality of sources radiate in cycles so that an alternation cycle of the plurality of sources is short relative to the CT rotation or scanning time. For example, the cycle frequency is in the order of kilocycles per second (KHz).

Optionally, a plurality of sources are energized together but at least one is electrically blocked (due to electrostatic or electromagnetic forces). Optionally, at least one source is electro-mechanically, pneumatically, or mechanically blocked and unblocked.

In exemplary embodiments of the invention, the detector, or a part thereof, or a dimension thereof, is substantially perpendicular to the beam center of at least one of the radiation sources.

In some embodiments of the invention, the cone beam is asymmetrical. In some embodiments an edge of each cone is substantially perpendicular to a detector row, generally the row on the same axial end of the detector as the source. In other embodiments the edge of the cone is not perpendicular, but extends outward from the center by 1-3 degrees. However, this small amount of deviation causes less than 10% of irradiated length of center line which is not reconstructed, under normal conditions.

In exemplary embodiments of the invention, the detector is substantially planar. In exemplary embodiments of the invention, the detector is curved. Optionally, the detector forms all or part of a circular cylinder or a sphere.

In exemplary embodiments of the invention, the plurality of radiation sources, and optionally the common detector, rotate around the subject, substantially about the CT rotation axis. In other exemplary embodiments of the invention, the subject rotates about the rotation axis (for example, in industrial applications).

In exemplary embodiments of the invention, attenuation data from the multiple sources are weighted for volume elements to provide data for reconstruction, as is well known in the art of cone beam reconstruction, for example, using the above referenced paper by Kohler, et al. Optionally, the weight is responsive to the path of the respective radiation beam to the detector and/or the volume. Optionally and additionally, the weight is responsive to the angle and/or the length of the path.

In exemplary embodiments of the invention, reconstruction methods known in the art are employed using data acquired from the detector due to attenuated radiation irradiated on a region by at least two radiation sources. Optionally and additionally, the acquired data is weighted responsive to a radiation source.

An aspect of some embodiments of the invention relates to a vacuum enclosure containing a cathode assembly. The vacuum enclosure also contains at least two target areas for electron beams emitted from the cathode assembly. Two or more voltage gates and/or grids are situated between the cathode assembly and the target areas. In an exemplary embodiment of the invention, each gate comprises a grid assembly adapted to operate in at least two modes. In a first mode, when electrified to a first voltage, the grid assembly provides a negative voltage relative to the cathode of sufficient strength to block a projected electron beam to the associated target. When electrified to a second voltage the grid assembly directs a beam at its respective target to generate X-rays from the selected target.

In an embodiment of the invention, the targets are on separate anodes. Alternatively, they are on the same anode structure.

In an embodiment of the invention, a single cathode is employed. Alternatively, the cathode assembly comprises two adjacent cathodes facing in directions, each adapted to emit a beam toward its associated target.

An aspect of some embodiments of the invention relates to an anode structure for the generation of X-rays from two targets. According to this aspect, the targets face each other. That is to say that they are situated at positions on an anode or anodes such that the interior angle between of the normal to the surfaces of the anode or anodes on which they are situated is between 0° and less than 180°. It should be understood that an interior angle of 180° corresponds to the two surfaces directly facing each other and that 0° correspond to the surfaces being parallel. In various embodiments of the invention the interior angle is between 45° and 135°, more preferably between 75° and 105°. Where the normals do not intersect, the interior angle is defined as the interior angle of the projections of the two normals on a plane situated halfway between the two normals. In actual design of interest the angle will be around 150-170 Deg, far from 75-105.

In an embodiment of the invention the X-ray beams formed on the two targets which face each other generate overlapping X-ray beams.

In some embodiments of the invention that incorporate both embodiments a single cathode is used to irradiate both targets, which face each other.

In an exemplary embodiment of the invention, alternate direction of the beam at the two targets alternately generates X-rays from the selected target. In an exemplary embodiment of the invention, alternation occurs at 1-5 kHz or lower or higher frequencies, depending on the application to which the tube is applied. In some embodiments e.g. when the tube is used in fluoroscopy systems switching frequency may be 25/30 or 50/60 Hz or similar frequencies.

An embodiment of the invention incorporates a modulation mechanism which alternately applies negative high voltages to at least one of two or more voltage gates. In an exemplary embodiment of the invention, application of the negative high voltage to a gate serves to "close" the gate with respect to an incident electron beam. Conversely, a gate to which a lower (optionally zero) voltage is applied is "open" with respect to an incident electron beam. Optionally, the lower voltage is applied to a gate to focus the electron beam to a desired degree with respect to a selected anode. Optionally, the gate is comprised of multiple electrodes and differential electrification of the electrodes serves to shift the beam (and X-ray source) slightly, in the manner of Shoval or one of the other references which provide more than one source, in a single vacuum envelope by steering the beam as referenced above.

In an exemplary embodiment of the invention, one or more closed gates prevent transmission of an electron beam to one or more anodes in an X-ray tube while one or more open gates permit transmission of an electron beam to one or more anodes in the same X-ray tube.

In an exemplary embodiment of the invention, a single X-ray tube comprising a cathode assembly, two or more targets on a one or more anodes and voltage gates interposed between them generates overlapping cones of X-ray beams. Optionally, the overlap is volumetric and not temporal.

Optionally, control circuitry regulates a duty cycle of the voltage gate. In an exemplary embodiment of the invention, the control circuitry synchronizes duty cycles of two voltage gates to provide oscillation between the gates. Optionally, the control circuitry synchronizes duty cycles of three or more voltage gates to provide rotation, or any other program, between the gates.

In an embodiment of the invention an X-ray tube of the invention is used as a source of X-rays for a CT scanner, such as that described in the applications incorporated by reference in the background applications section and in the present application.

In various embodiments of the invention the distance between the targets varies from about 5 cm to 10, 15 or more cm. An effective lower bound between the targets is provided by the need to have the cathode and grid structures substantially between the targets. The actual distance is dependent on the use for the tube. For cardiac CT applications, such as that described herein, 7-12 cm is a desirable distance range, since this allows for the acquisition of projection data for the heart during a single rotation of the tube around the patient. For other applications and for industrial applications, smaller distances may be appropriate.

In an exemplary embodiment of the invention, when used in some CT applications described herein, the cone beam is asymmetrical, with the smaller angle toward the heel of the anode. This allows for a smaller anode angle and an increased area of impingement on the anode for the same effective spot size. This allows for increased peak power handling. In a typical CT application each anode angle could be 5-10 deg, filament length 4-10 mm, effective focal spot size viewed at rotation plan 0.6-1.5 mm. Power rating depends on Anode diameter and rotation speed. In general, for CT applications a power rating of 80 kW is considered to be suitable. However, for the dual spot tube, the rating per target may be as low as 40 kW. In other applications the beams are symmetrical.

In an exemplary embodiment of the invention, spatial and/or temporal distribution of an electron beam from a cathode among two or more anodes contributes to a reduction in heat load on the anodes.

There is thus provided, in accordance with an embodiment of the invention, a method for CT cone beam scanning, comprising:

(a) relatively rotating a plurality of alternating cone beam radiation sources to an object, the sources being spaced parallel to the rotation axis, and radiating through a common portion of the subject onto a common detector array having axially spaced rows of detector elements, wherein the number of rows is greater than the number of plurality of sources; and (b) acquiring from at least a part of the detector, data responsive to radiation attenuated by at least part of the common volume of the subject irradiated by the plurality of radiation sources by at least a factor of two.

Optionally, the method comprises (c) reconstructing an image of the subject where the image of at least part of the common volume of the subject is reconstructed from attenuation data originating from a plurality of radiation sources.

In an embodiment of the invention, the data is acquired in a single rotation or less of said sources relative to subject.

There is further provided, in accordance with an embodiment of the invention a method for CT cone beam scanning, comprising:

(a) relatively rotating a plurality of alternating cone beam radiation sources to an object, the sources being spaced parallel to the rotation axis, and radiating through a common portion of the subject onto a common detector array having axially spaced rows of detector elements;

(b) acquiring from at least a part of the detector, data responsive to radiation attenuated by at least part of the common volume of the subject irradiated by the plurality of radiation sources; and (c) reconstructing an image of the subject where the image of at least part of the common volume of the subject is reconstructed from attenuation data originating from a plurality of radiation sources, wherein said image is acquired in a single rotation or less of said sources relative to subject.

In an embodiment of the invention, the image is the image of a beating human heart.

In an embodiment of the invention, substantially all of the radiation illuminating the object is used in the reconstruction.

Optionally, the patient is stationary during said acquiring.

Optionally, the plurality of sources comprises two or three sources.

In an embodiment of the invention, acquiring data is limited to a period of rotation of 220 degrees or less.

In an embodiment of the invention, all of the rows are illuminated by each of the sources. Alternatively, fewer than all of the rows are illuminated by both sources. Preferably, at least one source illuminates each row.

In an embodiment of the invention, cone beams from at least two sources are asymmetrical respective of the source trajectory plane.

In an embodiment of the invention, one edge of the asymmetrical cone beam is perpendicular to the detector array. Alternatively or additionally, the cone beams from at least one source is symmetrical respective of the source trajectory plane.

In an embodiment of the invention, the method includes alternately energizing the radiation sources. Optionally, the plurality of sources radiate in cycles so that an alternation cycle of the plurality of sources is short relative to the CT rotation or scanning time.

In an embodiment of the invention, data is acquired in synchronization with a signal, optionally at least one of an ECG signal or blood pressure signal.

In an embodiment of the invention, X-ray sources revolve around the object a plurality of times. Optionally, data is collected during said plurality of rotations. Optionally, data from different revolutions is averaged to reduce the noise in a reconstructed image. Optionally data from different revolutions is binned to form data from a given portion of a heart cycle and wherein said binned data is used to reconstruct a heart. Optionally, the data is used to reconstruct a plurality of periods within a heart cycle.

In an embodiment of the invention, rotationally moving comprises moving the radiation sources around the subject.

There is further provided, in accordance with an embodiment of the invention a method for CT cone beam scanning, comprising:

(a) relatively rotating a plurality of alternating cone beam radiation sources to an object, and radiating through at least one detector array having axially spaced rows of detector elements;

(b) acquiring from at least a part of the at least one the detector, data responsive to radiation attenuated by at least part of the common volume of the subject irradiated by the plurality of radiation sources by at least a factor of two; and (c) reconstructing an image of the subject where the image of at least part of the common volume of the subject is reconstructed from attenuation data originating from a plurality of radiation sources, utilizing substantially all of the radiation as defined herein.

There is further provided, in accordance with an embodiment of the invention, apparatus for CT cone beam scanning, comprising:

a table for holding a subject;

a gantry;

a first detector array, having a given number of rows of detector elements spaced along an rotation axis of the gantry, mounted on the gantry;

a first plurality of X-ray sources mounted on the gantry for rotation about the patient table on a rotation axis, the number of rows being at least twice the number of sources; and a controller that acquires data responsive to radiation from the sources from the detector array attenuated by at least part of the common volume of the subject irradiated by the plurality of radiation sources.

In an embodiment of the invention, the controller reconstructs an image of the subject where the image of at least part of the common volume of the subject is reconstructed from attenuation data originating from a plurality of radiation sources. Optionally, the controller is adapted to reconstruct said data acquired in a single rotation or less of said sources relative to subject.

There is further provided, in accordance with an embodiment of the invention, apparatus for CT cone beam scanning, comprising:

a table for holding a subject;

a gantry;

a first detector array, having a given number of rows of detector elements spaced along an rotation axis of the gantry, mounted on the gantry;

a first plurality of X-ray sources mounted on the gantry for rotation about the patient table on a rotation axis; and a controller that acquires data responsive to radiation from the sources from the detector array attenuated by at least part of the common volume of the subject irradiated by the plurality of radiation sources and reconstructs an image of the subject where the image of at least part of the common volume of the subject is reconstructed from attenuation data originating from a plurality of radiation sources and acquired from data acquired over a single rotation or less of said sources relative to subject.

In an embodiment of the invention, substantially all of the radiation illuminating the object is used in the reconstruction.

In an embodiment of the invention, the plurality of sources comprises two or three sources.

In an embodiment of the invention, acquiring data is limited to a period of rotation of 220 degrees or less.

Optionally, all of the rows are illuminated by each of the sources. Alternatively, fewer than all of the rows are illuminated by both sources. Optionally, at least one source illuminates each row.

In an embodiment of the invention, the cone beams from at least two sources are asymmetrical respective of the source trajectory plane. Optionally, one edge of the asymmetrical cone beam is perpendicular to the detector array.

In an embodiment of the invention, the cone beams from at least one source is symmetrical respective of the source trajectory plane.

In an embodiment of the invention, the controller includes a power supply alternately energizing the radiation sources.

In an embodiment of the invention, the plurality of sources radiate in cycles so that an alternation cycle of the plurality of sources is short relative to the CT rotation or scanning time.

In an embodiment of the invention, the apparatus includes:

a second detector array, having a given number of rows of detector elements spaced along an rotation axis of the gantry, mounted on the gantry;

a second plurality of X-ray sources mounted on the gantry for rotation about the patient table on a rotation axis, the number of rows being at least twice the number of sources; and a controller that acquires data responsive to radiation from the sources from both the first and second detector arrays attenuated by at least part of the common volume of the subject irradiated by the plurality of radiation sources.

In an embodiment of the invention, the second detector array and the second plurality of X-ray sources are circumferentially offset from the first detector array and first plurality of X-ray sources.

Optionally, the second detector array and the second plurality of X-ray sources are not axially offset from the first detector array and first plurality of X-ray sources.

In an embodiment of the invention, the first and second X-ray sources comprise sources axially spaced by a given distance and wherein the second plurality of X-ray sources are axially offset from the first plurality of X-ray sources by an amount equal to one-half the given distance.

In an embodiment of the invention, the first and second X-ray sources comprise sources axially spaced by a given distance and wherein the second plurality of X-ray sources are axially offset from the first plurality of X-ray sources by an amount equal to the given distance.

In an embodiment of the invention, the first and second X-ray sources comprise sources axially spaced by a given distance and wherein the second plurality of X-ray sources are axially offset from the first plurality of X-ray sources by an amount equal to twice the given distance. Optionally, the plurality of sources comprise two symmetrical cone beam sources.

BRIEF DESCRIPTION OF THE DRAWINGS

Non-limiting examples of embodiments of the present invention are described with reference to figures listed below. Equivalent structures, elements or parts that appear in some figures are labeled with the same numerals. Dimensions of components and features shown in the figures are chosen for convenience or clarity of presentation and are not necessarily shown to scale, except where indicated.

DETAILED DESCRIPTION OF EMBODIMENTS OF THE INVENTION

In this application the terms "grid" and "gate" refer both to electrostatic electrodes used to affect the electron beam traveling from the cathode to anode in X ray tubes.

Figure 1:
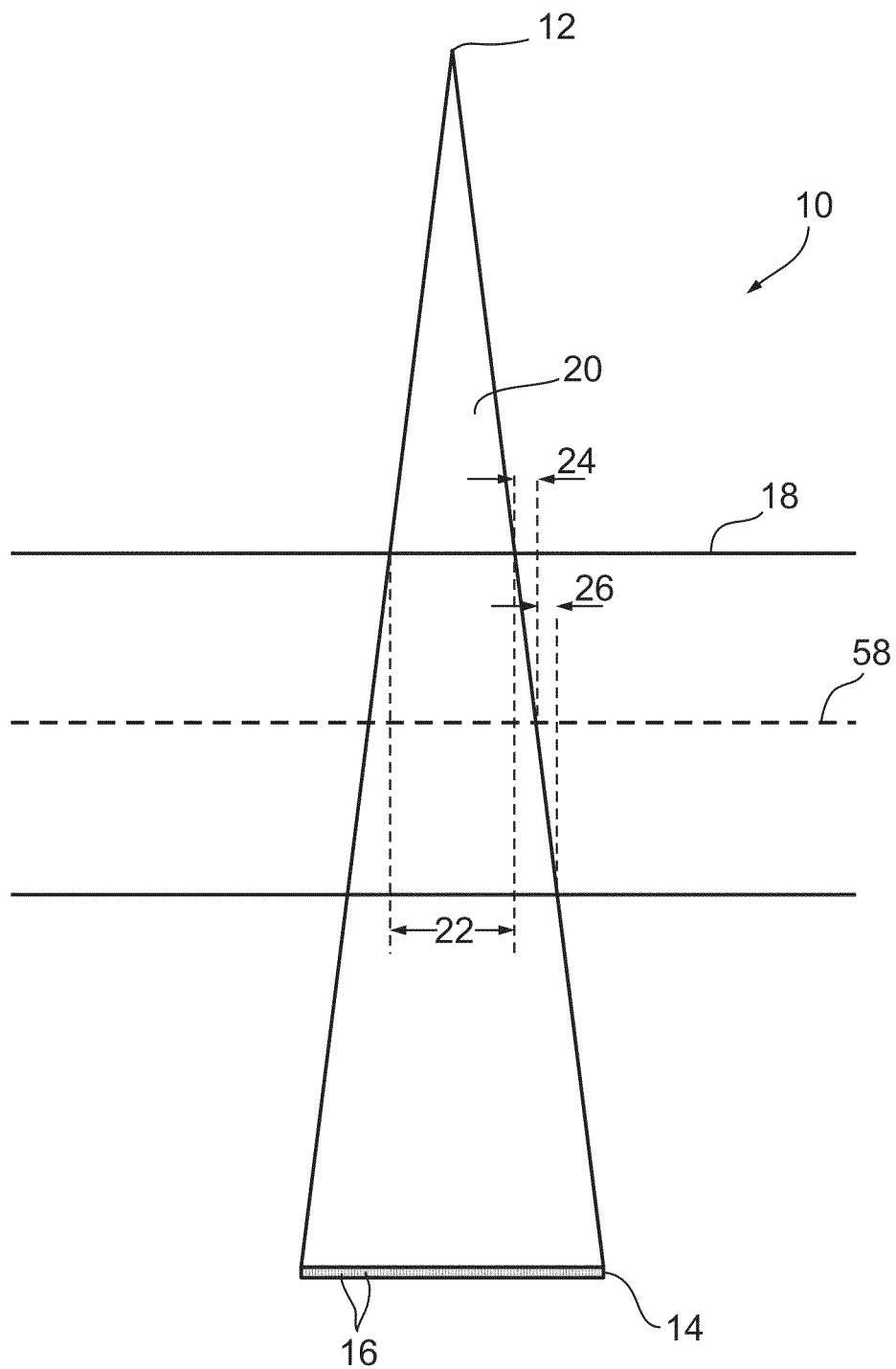
FIG. 1 shows a single cone beam system of the prior art having a single source and a detector array.
Figure 2:
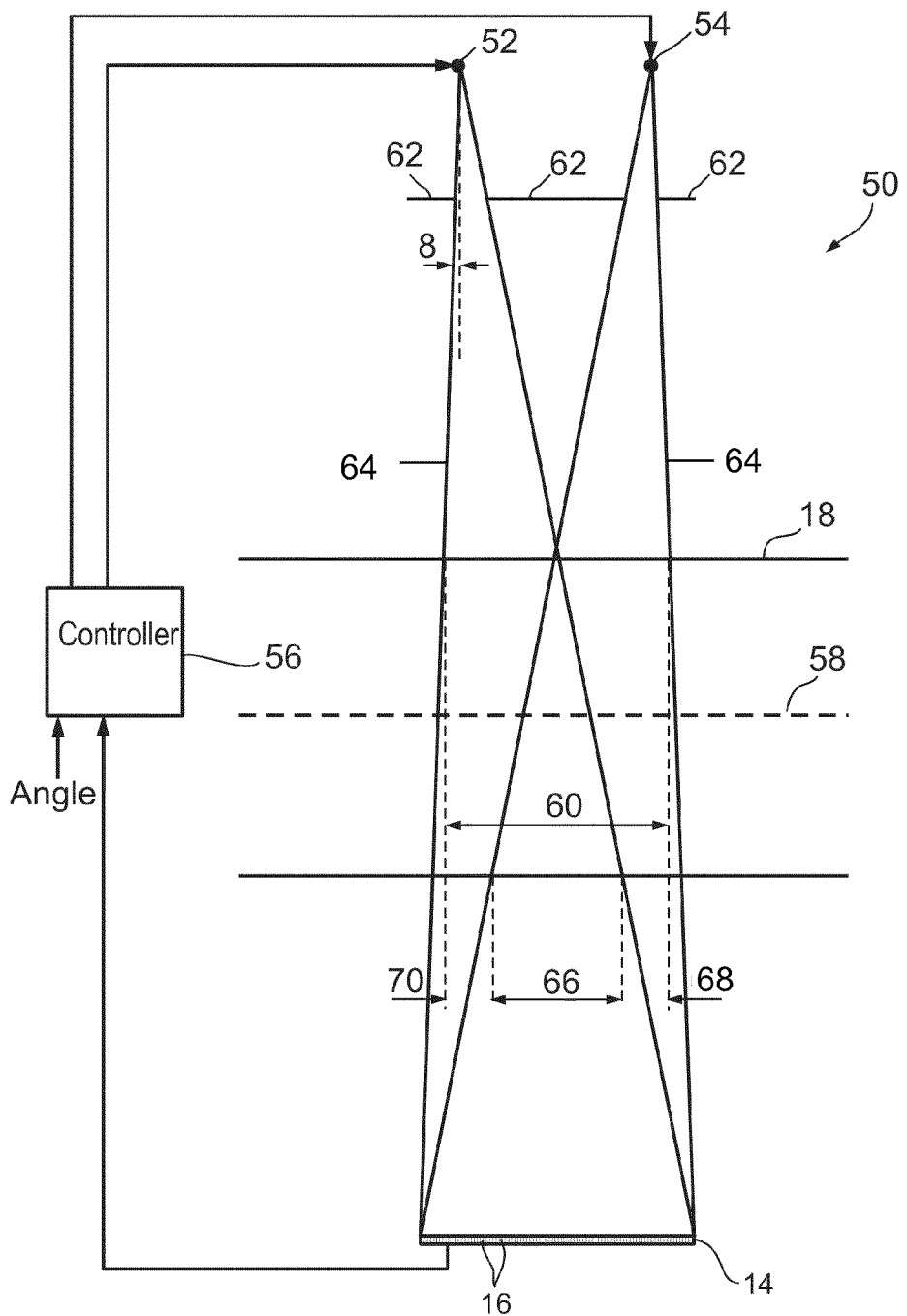
FIG. 2 is a view similar to that of FIG. 1, showing the use of two sources to reduce radiation to the patient while providing complete data in a half rotation, in accordance with an exemplary embodiment of the invention.

FIG. 2 is a view similar to that of FIG. 1, showing a system 50 utilizing two sources 52 and 54 to apply radiation to patient while providing attenuation data in a half rotation of the sources or optionally a larger rotation angle, in accordance with an exemplary embodiment of the invention. FIG. 2 is to scale. For simplicity the support structures holding the sources 52 and 54 as well as other parts of system 50 are not shown.

As shown in FIG. 2, the beams both illuminate the entire axial extent of detector 14, when they are energized. A controller 56 controls the rotation of the sources and detector array 14 about an axis 58 and alternately energizes sources 52 and 54 and acquires data from the detectors that form a part of detector array 14. Data from the detectors, together with the rotation angle at which the data was acquired and the source corresponding to the data is stored and used to reconstruct a CT image of a region 60.

Collimator 62 limits the extent of the beams so that the beams irradiate the patient only within the solid angles covered by detector array 14. Collimator 62 may be fixed relative to the sources 52 and 54 and detector 14 or it may be provided with means to move the collimator leafs so as to change the geometry of the cone beams. In particular, in one mode of operation, one of the sources e.g. 52 is blocked and one source e.g. 54 is used to irradiate subject 18 in the manner of the prior art CT of FIG. 1.

Further, in some embodiments sources 52 and 54 can be moved axially to a different position relative to detector 14. For example, if the sources are moved by half the source to source distance or source 52 is centered about the detector, source 54 is blocked and collimator 62 is adjusted appropriately, the scanner can be used in the prior art single symmetric cone beam mode.

Region 60 can be divided into three parts. In a first region 66 data is acquired from radiation by both sources 52 and 54. In regions 68 and 70 data is acquired only from beams 52 or 54 respectively. In region 66, the image is reconstructed utilizing data collected from both beam, in as much as data is available from both sources for a particular volume element at a particular gantry angle. Though the setup may not fully meet the Tuy-Smith condition, and data in region 60 may still be incomplete and somewhat truncated, still—given other resources and conditions substantially equivalent—better images with less cone beam artifacts may be generated as compared to a single source cone beam scanner as shown in FIG. 1 performing a circular trajectory of the source.

In regions 68 and 70, the data from the respective single beam is used for reconstruction. In these regions the distance of any volume element from the source trajectory planes are small and data incompleteness is minimal.

Axis 58 can be centered between the sources and detector to give a magnification of 2. Optionally, the center of rotation can be offset from the center to give lesser or greater magnification. It is understood that while the magnification may be varied, the total extent of the imaged region depends on the distance between the sources, the geometry of collimator 62 and the coverage of detector array 14.

While in the embodiment shown in FIG. 2, some radiation is not utilized for reconstruction, the volume irradiated without producing image is substantially smaller as compare to the prior art geometry shown in FIG. 1.

In a non limiting exemplary embodiment the distance of sources 52 and 54 from the rotation axis is 500 mm and the spacing between the sources is 100 mm. Detector 14 includes 160 rows of detector elements with spacing of 1 mm between rows centers. The rows extend in the radial direction as parallel concentric arcs at a radius of 900 mm from the source to source axis (the detector is shown as being flat in the axial direction, in all the figures, for simplicity). The magnification of the system in this example is 1.8. For a scanned subject 18 with diameter of 250 mm, the covered length 60 in one rotation is 125 mm. The outside angle 8 is then 1.909 degrees.

The width of the overlap region 66, where at least for some rotation angles data is available from both sources, is 108.4 mm. The width of regions 68 and 70 where data is available for all rotation angles from one source only is 10.1 mm, for a total full coverage region of 118.5 mm. The width of the beam at the exit is 128.6. The sources are rotating at a frequency of four rotations a second about the subject. 1500 views are acquired from detector 14 for each rotation and the sources 52 and 54 are energized alternatively under control of control unit 56 at a frequency of 3 KHz so each source generates 750 sets of data for each rotation. For a partial rotation of about 200°, 418 sets of data are acquired for each source.

In some embodiments of the invention (as in the above example and as shown in FIG. 2), beam edges 64 may diverge away from the sources. Under these circumstances some of the radiation may not be used in reconstruction. In the exemplary embodiment of the invention above about 93% of the length irradiated along the scanner axis is used in reconstruction from a single rotation (region of full coverage). In other embodiments with different configurations, the ratio may vary between 100% and 80%. In comparison, a prior art cone beam CT according to FIG. 1 with similar geometrical distances, subject 18 diameter of 250 mm and entry width 22 of 125 mm, only about 75% of the irradiated length at the scanner center is used for reconstruction. In some embodiments the multiple cone beams may be symmetrical respective of the source trajectory plane of each, wherein the inner parts of the cone beam are overlapping for at least a part of the irradiated volume. It is noted that as the length and diameter of the irradiated area increase, the percent of length reconstructed increases for the various embodiments (if the sources are moved further apart) and decreases when a single source of the prior art is used. In addition, the size of the detector array of the prior art increases in size at a faster rate than those of the present invention.

Figure 3:
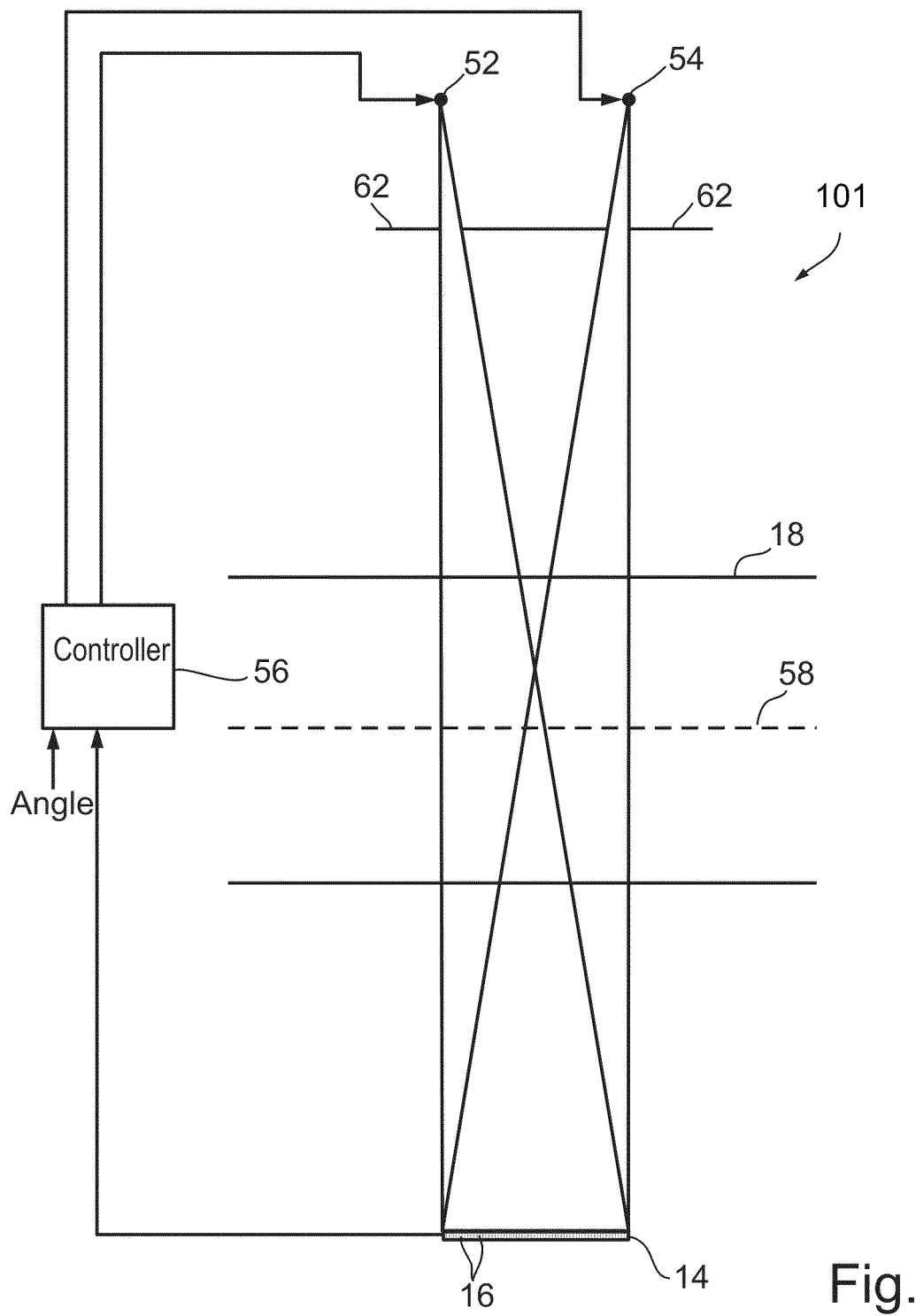
FIGS. 3 and 4 show variations on the embodiment of FIG. 2.

FIG. 3 show a system 101 similar to system 50 in FIG. 2 wherein the distance between sources is approximately the same as the axial extent of detector 14. System 101 maximizes the utility of radiation. It is noted that the inner edges of the beams from the sources cross inside the region of reconstruction. This does not cause serious reconstruction problems, since views are taken from all angles so long as a 360 degree rotation is performed.

Furthermore, while in FIGS. 2 and 3 each of the beams is shown as illuminating the entire detector array, in some embodiments of the invention, a portion of the array may be illuminated by only one of the beams.

Figure 4:
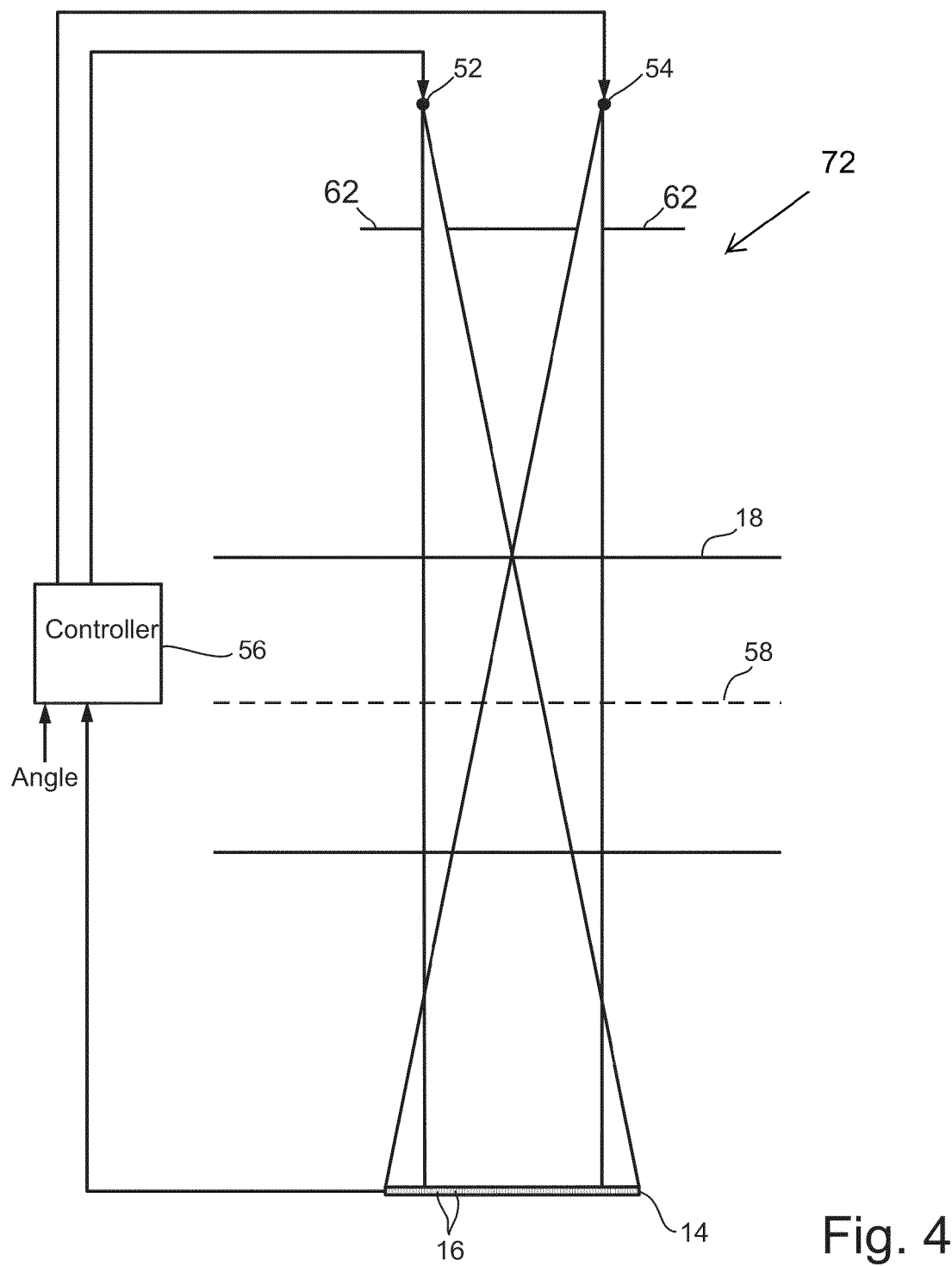

FIG. 4 shows a system 72 similar to that of FIG. 3 and on the same scale, in which the detector is extended so that a 180 degree plus rotation can provide a full data set. In system 72, the beam angle of the beams is increased. The detector size is increased to correspond to the inner edge of the beam. This allows for full coverage of the region of full coverage on a half rotation.

In other embodiments where the diameter of the reconstruction area is larger or small than that shown, the cone beam and area of the detector that is illuminated can be adjusted to change the amount of radiation to the patient and/or amount of rotation needed for a complete data set. Furthermore, where the magnification is changed by changing the position of the reconstructed portion and center of reconstruction, the illumination of the detectors may vary between a situation in which the outer portions of the detectors are illuminated by only the beam opposite (as for example where the magnification is low and the center of rotation is moved toward the detectors) and the situation shown in FIG. 4. In some cases the detector is illuminated over its entire length by both beams.

It is understood that the collimators can be used to shape the inner angles of the beams to provide an optimum angle, in some embodiments of the invention.

In exemplary embodiments of the invention, a variation of the cone beam angle and offset will effect the reconstructed volume in patient 18.

The detector elements that make up detector array 14 can comprise any detection elements as known in the art, for example, comprising $CdW_4$ crystals coupled to Silicon photodiodes detection, or any other radiation detection scheme suitable for CT as known in the art.

Figure 5:
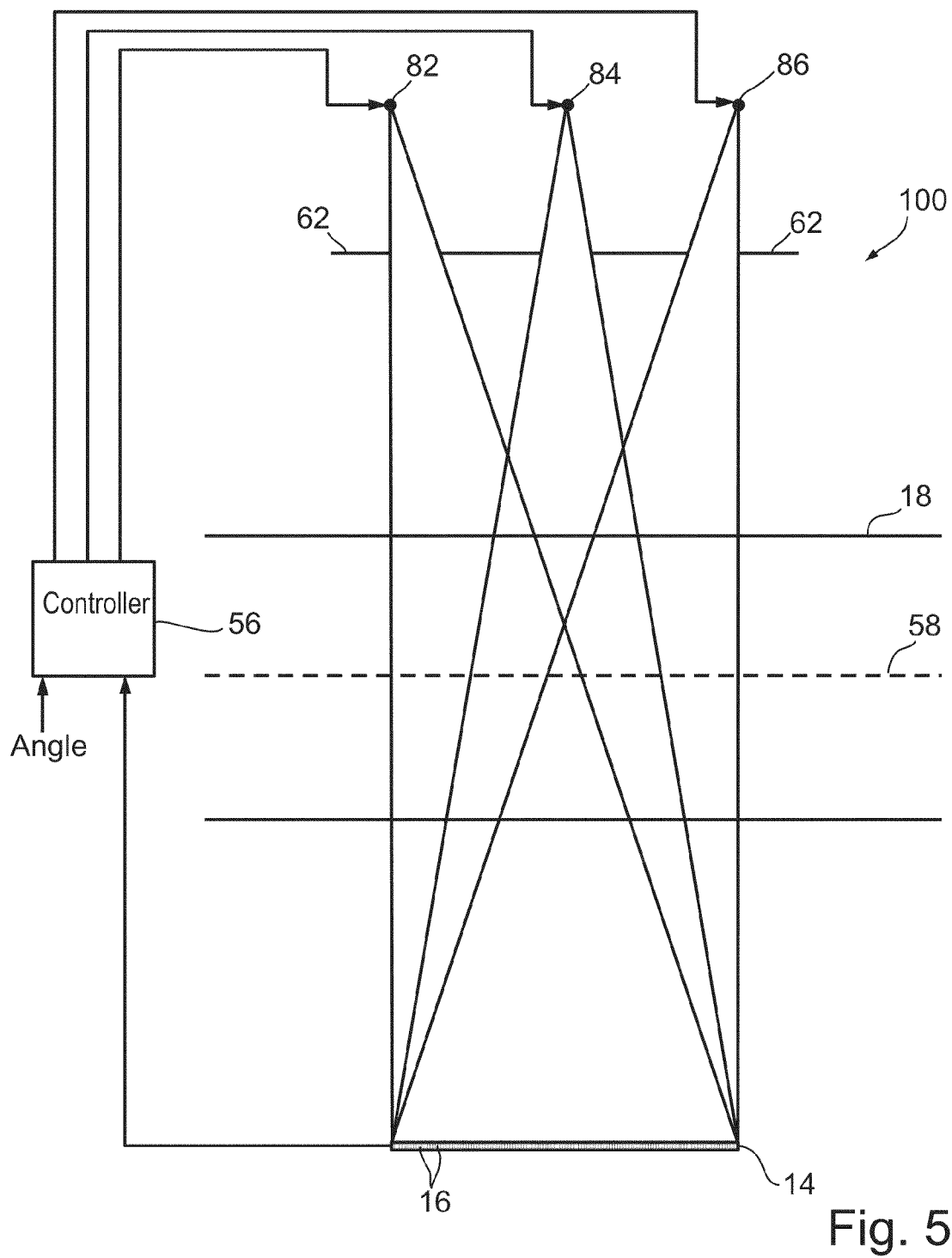
FIG. 5 schematically illustrates a side view of a setup of a CT scanner similar to that shown in FIG. 3, comprising three cone beam sources, in accordance with exemplary embodiments of the invention.

FIG. 5 schematically illustrates a CT scanner 100 similar to 50 of FIG. 2, comprising three cone beam sources 82, 84 and 86. The offsets between the sources are not necessarily equal.

Figure 6:
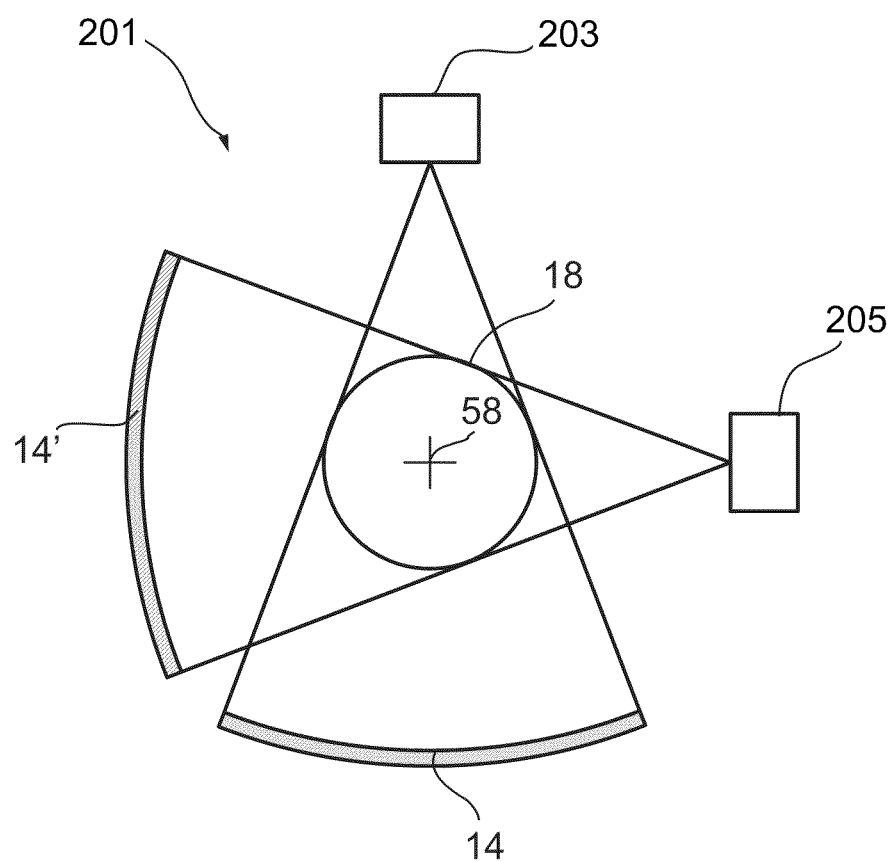
FIG. 6 schematically illustrates a trans-axial view of a CT scanner having circumferentially offset groups of sources, in accordance with exemplary embodiments of the invention.

FIG. 6 schematically illustrates a cross-section trans axial view of a CT scanner 201 comprising a group of multiple cone beam sources 203, 205 offset from each other circumferentially about rotation axis 58, each with a corresponding detector array 14 and 14', respectively, in accordance with exemplary embodiments of the invention. It should be understood that preferably each of multiple cone beam sources comprises two or more axially offset sources as shown in FIGS. 2-5. It should be understood that larger number of multiple cone beam sources can be provided, e.g. 3 groups or more and the groups can disposed about the rotation angle at equal angular spacing or at other angular positions.

Further, in FIG. 6 the detector arrays are shown to be rotating along with the sources but in some embodiments a fixed array of detectors is provided where the sources are rotated. To reduce effects of scattered radiation originated from one multiple cone beam source and impinging on the detector corresponding to another multiple cone beam source, anti-scatter grids are provided in front of the detectors as known in the art. In addition, sources 203 and 205 may be energized alternatively, in addition to the switching of radiation between cone beams within each multiple source.

In some embodiments described by FIG. 6 the multiple sources 203 and 205 are mounted at a same axial position relative to the scanned subject. Thus, for example if source 203 emits two alternating axially spaced cone beams and source 205 emits two alternating axially spaced cone beams, each focal spot in source 203 moves in rotation on a same circular trajectory as a corresponding focal spot on source 205. Each of the corresponding pairs of focal spots moves on a parallel trajectory with the other pair of corresponding focal spots. In one mode of operation data collected by detector 14 while the sources are rotated over rotation angle smaller than needed for image reconstruction is added to data collected by detector 14' alone during the same time so as to form a data set useful for reconstruction. In this mode, temporal resolution is improved relative to system with one multiple source as in FIG. 2-5. In another mode of operation, data collected from detectors 14 and 14' is added or averaged to improve statistics and reduce image noise.

In some other embodiments included in FIG. 6 multiple sources 203 and 205 are displaced axially as well as circumferentially. Thus, for example if the axial displacement is equal to half the spacing between the focal spots, the focal spots of the two sources 203 and emits two alternating cone beams and source 205 emits two alternating cone beams, the four focal spots move on circular trajectories that are spaced by one-half the source spacing in each of sources 203 and 205, with the cone beams of the two sources interleaved. Parts of the subject 18 are irradiated by radiation from two or more focal spots and the corresponding image is reconstructed from weighted data acquired from multiple focal spots. This results in increased resolution.

Alternatively, if the centers of 203 and 205 are axially spaced by a same distance as the distance between the focal spots in each of 203 and 205, then an axial extent double that of a single unit can be imaged in one half rotation.

Alternatively, the axial spacing can be equal to twice the source distance. In this case the focal spots of the cone beams rotate on parallel trajectories that are one source distance apart. If, instead of the asymmetric cone beams shown above, the cone beams are symmetric, then the region between the sources 203 and 205 is irradiate by one cone beam from source 203 and one from source, 205 in much the same way as is the region between the focal spots on a same source 203 or 205. This results in a larger swath being scanned in each rotation.

Thus depending on the amount of axial displacement for the two sets of sources, faster data acquisition, higher resolution or a larger swath are possible.

Figure 7:
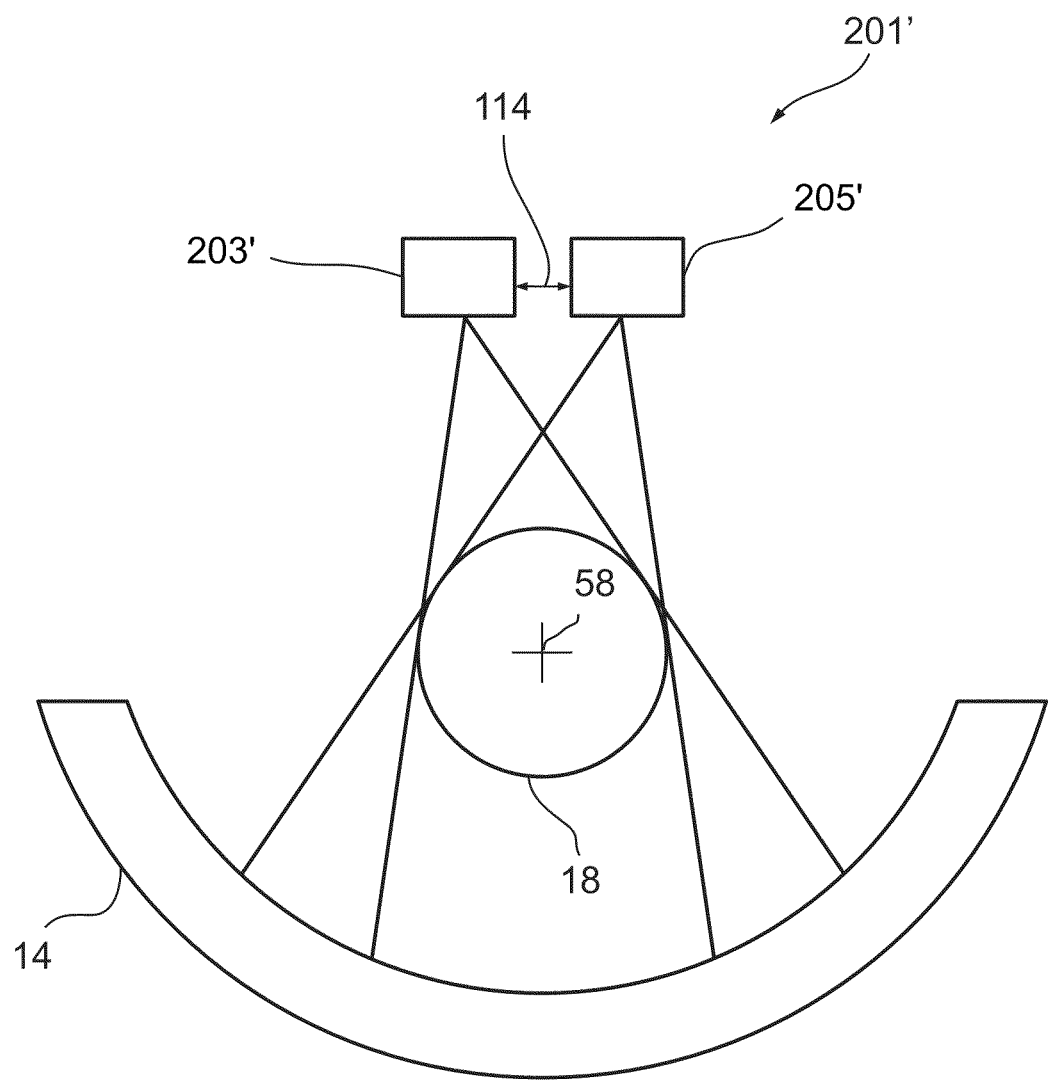
FIG. 7 schematically illustrates a trans-axial view of an alternative CT scanner having circumferentially offset groups of sources, in accordance with exemplary embodiments of the invention.

FIG. 7 schematically illustrates a cross-section trans axial view of an apparatus for CT scanner 201' comprising a group of multiple cone beam sources 203' and 205' offset from each other in a direction perpendicular to rotation axis 58, and sharing a common curved detector 14, in accordance with exemplary embodiments of the invention. It should be understood that preferably each of multiple cone beam sources comprises two or more axially offset sources as shown in FIG. 2, 3 or 4.

In some embodiments of the systems described in FIG. 2-7 each of the focal spots generating the cone beams is moved periodically during radiation, either between discrete positions or by periodic motion and data acquisition is synchronized to collect data separately for different focal spots position. Focal spot deflection can be accomplished by electrostatic or magnetic deflection of electron beam impinging on the anode surface. The use of focal spot deflection for improvement of image resolution is well known in the art as described e.g. in U.S. Pat. No. 4,637,040, the disclosure of which is incorporated inhere by reference. The focal spot deflection can be in the axial direction or in the trans-axial direction or both, providing improved resolution in the corresponding direction.

In exemplary embodiments of the invention, a CT scanner may comprise a plurality of configurations of the kind illustrated in FIGS. 2-7. Optionally, the scanner may comprise a combination of the configurations shown in FIGS. 2-7 or their variants. In exemplary embodiments of the invention, detector 14 comprises a cylindrical ring of fixed detectors while the sources rotate about rotation axis 58. Alternatively, both the sources and detectors are fixed and the object being imaged rotates. This construction is especially useful for industrial imaging.

Optionally, the sources and detector array 14 are connected rigidly. Optionally or alternatively, at least a portion of the movement of the sources and the detector array is synchronized substantially without a mechanical connection.

In exemplary embodiments of the invention, the sources are switched on and off sequentially, such that radiation is emitted alternatively by the sources. Alternatively, the sources are energized immediately after each other and then energized in a similar way as the sources pass fixed increment in their rotation about axis 58.

In exemplary embodiments of the invention, a sequence of X-ray emissions is generated such that all of the data is acquired when the heart is relatively quiescent, e.g. at a particular phase relative to the R signal of an ECG, by synchronization to an ECG or blood pressure signal. In exemplary embodiment of the invention the data is acquired as a heart cycle phase centered about 70% of the R-R interval or about another phase in the range of 65% to 75% of the R-R interval.

In exemplary embodiments of the invention, the sources (e.g., 52 and 54) radiate cyclically so that an alternation cycle of the plurality of sources is short relative to the rotation or scanning time. For example, in the order of kilocycles per second (kHz) as described below in more detail.

The relative rotational motion about axis 58 while irradiating subject 18 and acquiring data may comprise a full circle or a half circle or a half circle plus additional angular range or any other rotation angle as required for reconstruction of the object, as known in the art.

Further, in some embodiments of the invention the sources 52 and 54 are energized and data acquired for time extent comparable or exceeding a whole heart period. In exemplary embodiment the rotation speed is several rotations per heart beat and acquisition lasts for longer than a heart beat period. Images are reconstructed for data sets corresponding each to rotation angle as needed for image reconstruction with angular and temporal increment between the sets. Thus a sequence of images is generated, corresponding to successive phases in the heart cycle.

Further, in some embodiments of the invention the sources 52 and 54 are energized and data is acquired multiple times, during multiple heart periods wherein each single acquisition is over a rotation angle which is optionally smaller than needed for image reconstruction. Data from multiple heart beats acquired at a particular phase of the heart period are added together to form a data set for image reconstruction. These embodiments provide image acquired over a shorter part of the cardiac cycle thereby improving temporal resolution.

Further, in some embodiments of the invention the sources 52 and 54 are energized and data is acquired multiple times for a period of 180+ degrees, during multiple heart periods. Data from multiple heart beats acquired at a particular phase of the heart period are weighted according to redundancy and used together for image reconstruction. Alternatively, each data set is reconstructed to image and images are averaged. These embodiments provide images with reduced noise as required e.g. for large subjects wherein the radiation from sources 52 and 54 is highly attenuated and the data received by detector 14 has a high statistical error.

Optionally, the region of interest is completely covered by radiation from the sources and may be reconstructed by circular motion at one position relative to rotation axis 58. Optionally, data is acquired at one axial position, subject 18 is moved along rotation axis 58 and data is acquired at a second axial position, the sequence optionally repeated as required to cover the region of interest. Optionally said motion of subject is by less than the width covered by radiation in one position so parts of subject 18 are irradiated both at one subject position and at a second subject positions. The image of such overlap region may be reconstructed from weighted data acquired from different sources. Optionally, for this embodiment, the beams are symmetric and identical and the movement is twice the spacing between the sources. Then the form of the radiation between the second source in the first position and the first source in the second position is the same as the radiation between two sources at a same position.

In a non limiting exemplary embodiments of the invention useful for scanning the human heart, the source's focal points are separated by 120 mm (range 60 to 140 mm) at a distance 500 mm from axis 58 (SAD) (range 400 to 700 mm). Detector 14 comprises a circular arc with a radius of 900 mm (range 700-1000 mm) from the line connecting the focal points of the sources (SDD), so that all beam lengths are approximately the same. With this geometry, the system has a magnification of 900/500=1.8 (range 1.5 to 2.2). In an embodiment of the invention, detector 14 has an axial extent of 162 mm (range 100-250 mm) comprising 180 rows of 0.9 mm elements (range 0.5 to 1.5 mm, number of rows derived from extent and element size). Alternatively, smaller size elements may be provided, e.g. size 0.2 mm or 0.3 mm and in certain modes of operations element are binned together to generate summed output signal. The extent about the isocenter (rotation axis 58) is 120+(162−120)/1.8=143 mm. This extent may cover a whole heart or its substantial part in one scanning rotation.

For comparison, a similar geometry and magnification with a single source covering the same 143 mm extent about the rotation axis would require a detector with an extent of 143×1.8=257 mm and 286 rows, typically more demanding mechanically, more expensive and the reconstruction is more problematic as the cone angle is wider and more data is off the central beam, thus less conforming with the Tuy-Smith condition.

As for temporal resolution, assuming a heart rate at about 60 beats per second, or about 1000 ms per beat, a scan rotation of about 250 ms with at least 500 data samplings per rotation (for each source) may well capture the heart substantially as a snapshot (frozen), especially if the scan is synchronized with ECG or other signal to capture the heart just during a period of low movement.

Consequently, assuming a duty cycle of 50% for each source, each on or off time is 250/(500×2)=0.25 ms, and a switching rate of 2 KHz is required of each source.

Taking into account the two simultaneous scanning trajectories, a partial circular scan may be sufficient. Assuming a rotation about 220°, then the required scan time will be only 250×220/360=153 ms, enhancing the temporal resolution.

This radiation switching rate may be achieved, for example, by a tube with two or more anodes and one or more cathodes, where the electron flow from a cathode to an anode is alternated by an alternating negative potential applied to one or more grid electrodes. Another example is two conventional tubes with alternating high voltage supply which energizes the two tubes alternatively. Another example is by steering the electrons over one or more anodes.

Yet another example of apparatus for producing alternating radiation from two sources is to block and unblock the radiation paths of the beams mechanically and/or pneumatically and/or electro-mechanically, for example by perforated rotating wheel comprising of radiation blocking material such as lead or tungsten.

An exemplary X-ray tube for use in the present invention is described below. In the disclosed X-ray tube, the two sources are in the same vacuum enclosure and electron beams are gated by grid electrodes to one or the other source focal point.

The exemplary embodiments described above are examples of arrangement and operation of embodiments of the present invention, but are not limiting in any respect whatsoever and any parameter may be changed to achieve some performance, size or cost criterions.

Figure 8:
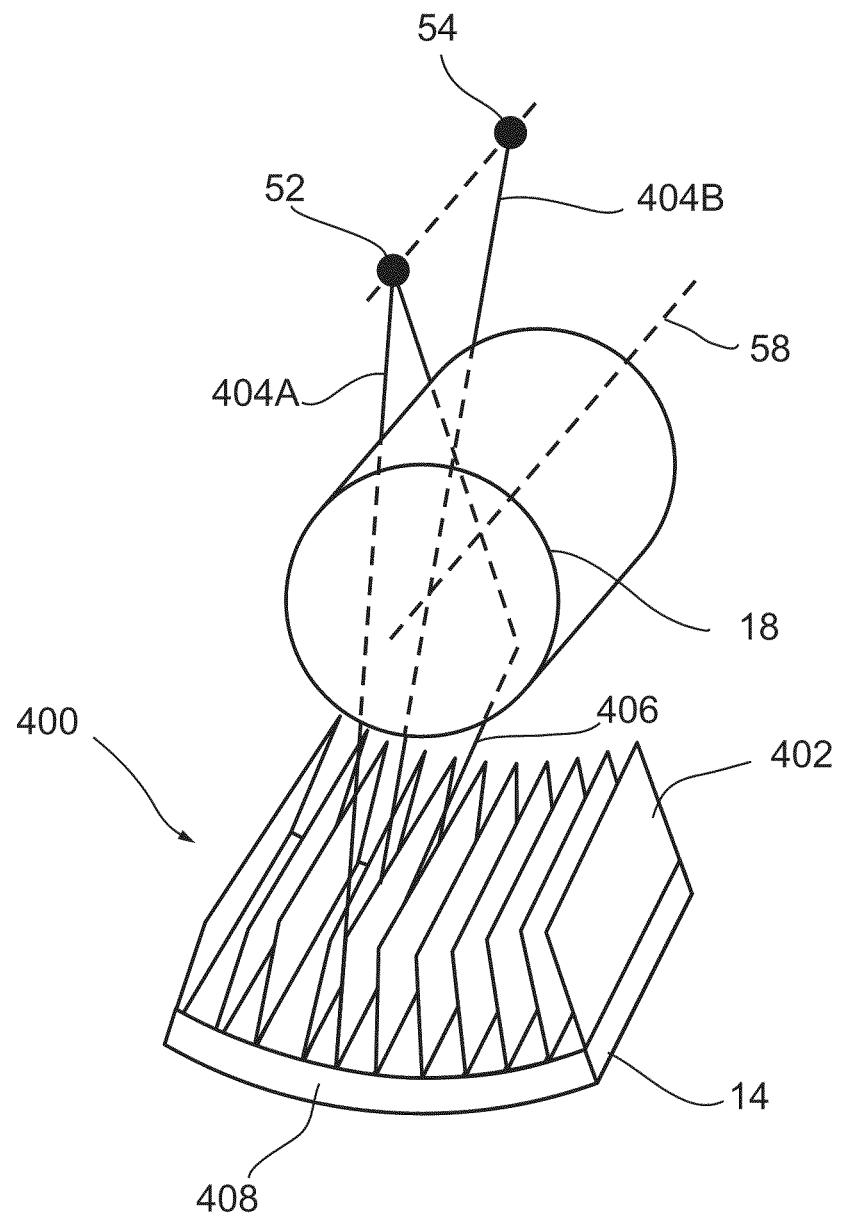
FIG. 8 schematically illustrates an anti-scatter grid with septa aligned parallel to the rotation axis, in accordance with an exemplary embodiment of the invention.

FIG. 8 schematically illustrates an anti-scatter grid 400 with septa 402 aligned substantially parallel to rotation axis 58 and radially to sources 52 and 54 axis.

Septa 402 allow direct radiation 404A from source 52 or 404B from source 54 to impinge on detector elements in detector column 408. Beams scattered by patient 18, such as beam 406 are blocked from impinging detector elements 408.

Optionally, grid 400 comprises a part of detector 14. Optionally or alternatively, grid 400 is attachable to, and optionally detachable from, detector 14.

Figure 9A:
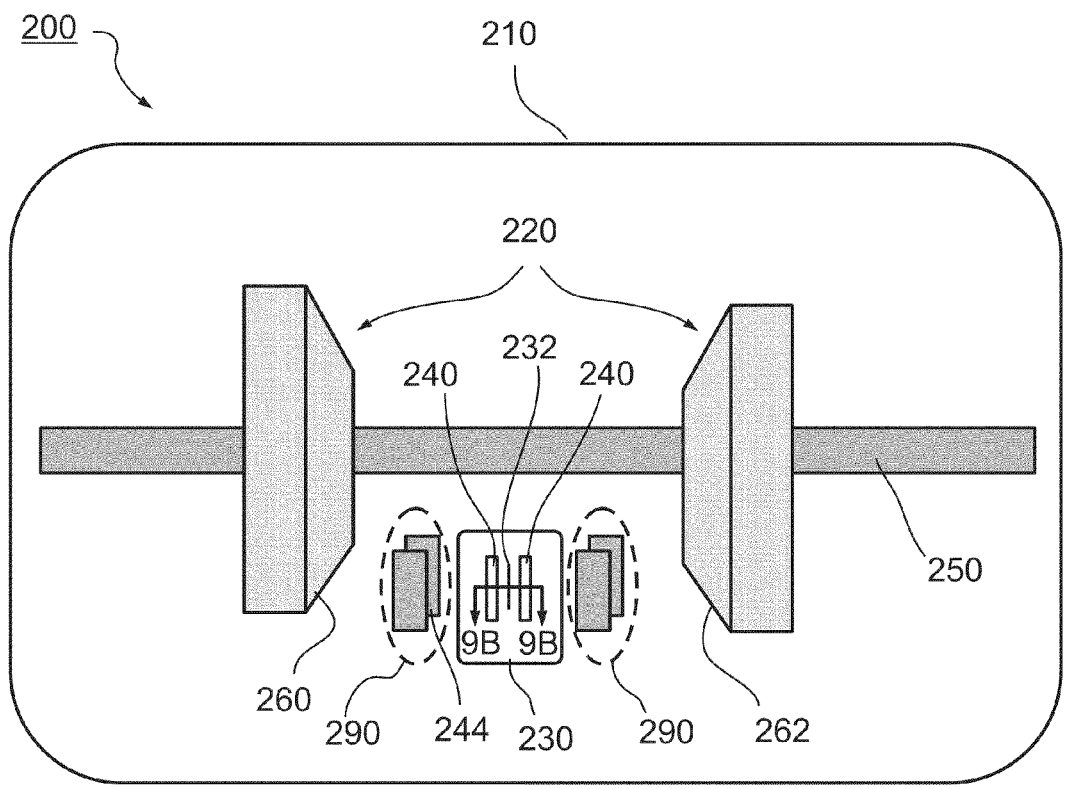
FIG. 9A schematically depicts relevant portions of an exemplary X-ray tube according to an embodiment of the invention.

FIG. 9A schematically depicts the relevant portions of an exemplary X-ray tube 200 according to an embodiment of the invention.

Figure 9B:
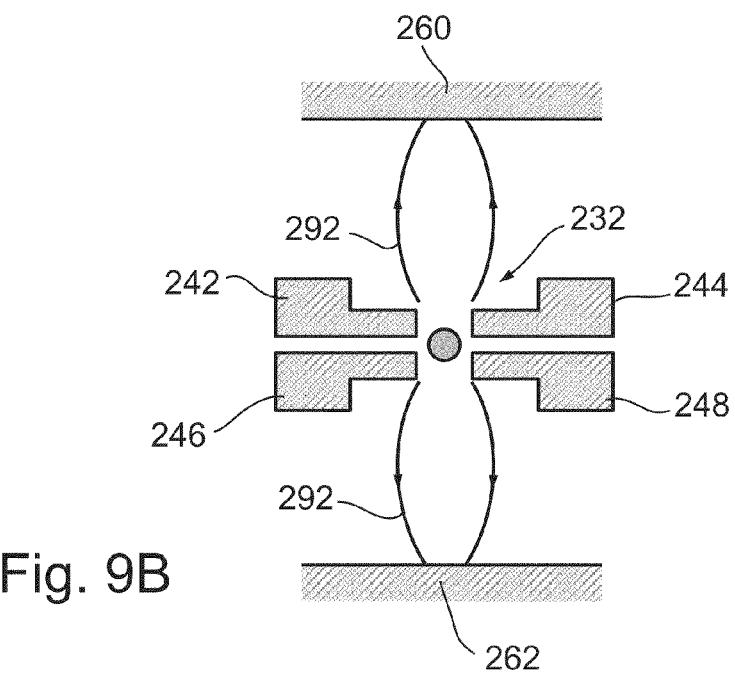
FIG. 9B is a cross-sectional view of the cathode assembly of FIG. 9A.

In the depicted embodiment, a single vacuum enclosure 210 houses two anodes 220 with a cathode assembly 230 positioned between them. FIG. 9B shows a cross-sectional view of the cathode assembly structure.

Optionally, anodes 220 are rotating anodes. In an exemplary embodiment of the invention, anodes 220 are mounted on a common rotation axis 250 within vacuum enclosure 210. For simplicity, the means for rotating the anodes are not shown. However, any method for rotating anodes in X-ray tubes, as known in the art, can be used. Similarly, the electrical connections of the anode(s) and cathode(s) are not shown for simplicity. Making such connections is well known in the art. Furthermore, any suitable construction of the anodes as known in the art can be used.

On one embodiment of the invention, cathode assembly 230 includes a single cathode filament 232. In one embodiment of the invention, the cathode is grounded, and the anode is at a high positive voltage. In others the anodes are grounded and the cathode is at a high negative voltage. Preferably, both the cathode and anode are electrified with negative and positive voltages respectively. This is preferred because it is easier to handle two voltages of (for example) 70 kW then one voltage of 140 kW. In any event, the difference in voltage between the cathode and anode depends on the application in which it is being used. For a medical CT application, the voltage is in the range of 80 kV and 140 kV. Heating of filament 232 causes cathode 230 to thermally emit electrons which form a cloud around the emitting surface of the cathode. The electrons, accelerated and impinging on targets 260 and 262 give rise to emission of X-rays. Vacuum 210 is provided with ports/windows relatively transparent to X radiation that allow X-ray beams to be emitted out of the enclosure. The shape and size of the ports determines the angular extent of the beams. Thus, the window opening (and external collimators) define the type of beam. For the present invention, the opening defines a cone beam with overlapping beams as shown in FIGS. 2-4.

In the depicted embodiment, voltage gates 240 are provides as part of cathode assembly 230 and are capable of modulating a beam of electrons that impinge targets 260 and 262 on anodes 220. The depicted configuration insures that a beam of thermally emitted electrons from filament 232 must pass the electrostatic field generated by gates 240 to arrive at targets 260 and 262. In an exemplary embodiment of the invention, each voltage gate 240 comprises a pair of electrodes (e.g. 242 and 244 or 246 and 248, as shown in FIG. 9B). Each pair of electrodes is electrically isolated from the filament. In some embodiments the electrodes within each pair are electrically connected. In other embodiments they are insulated from each other so there can be applied a bias voltage between them.

The gates and/or the cathodes may include additional electrodes to confine and/or to form the beam, as is well known in the art. These additional electrodes are depicted very schematically as a pair of plates 290 for each target. As indicated below electrodes 290 can be used for focusing, gating and other functions. For simplicity of presentation, electrodes 290 are shown only in FIG. 9A and are omitted from FIGS. 9B-E. However, such electrodes can be applied to any of the embodiments shown.

Two beams, very schematically shown at 292 in FIG. 9B are generally alternately generated as described below. The support structure of the elements is not shown, for simplicity of presentation. Optionally, only those portions of cathode 230 facing targets 260 and 262 are emitting. In an exemplary embodiment of the invention, the gates are connected to control circuitry 310; described below with reference to FIGS. 10A, 10B, 11A and 11B.

Figure 9C:
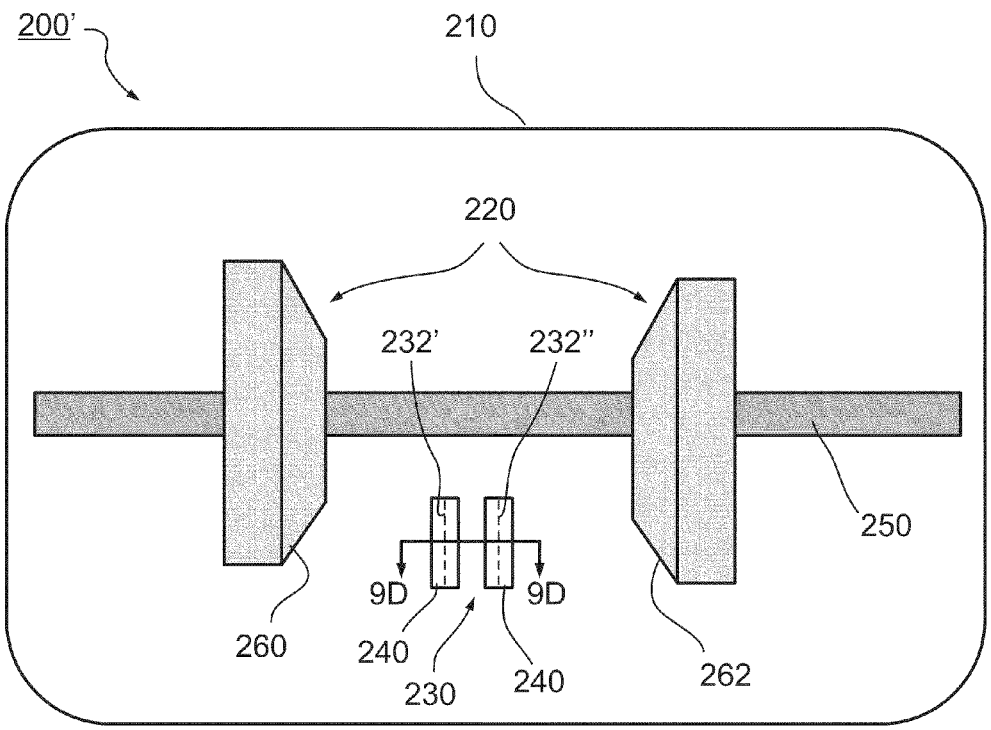
FIG. 9C schematically depicts relevant portions of an exemplary X-ray tube according to an embodiment of the invention.

FIG. 9C shows an X-ray tube 200' having an alternative cathode construction, in accordance with an embodiment of the invention. In this embodiment cathode assembly 230' has separate emitters 232' and 232" (each with its own filament) used to produce the electron beams that pass their respective gates 240. Alternatively, the cathodes can share a common filament.

Figure 9D:
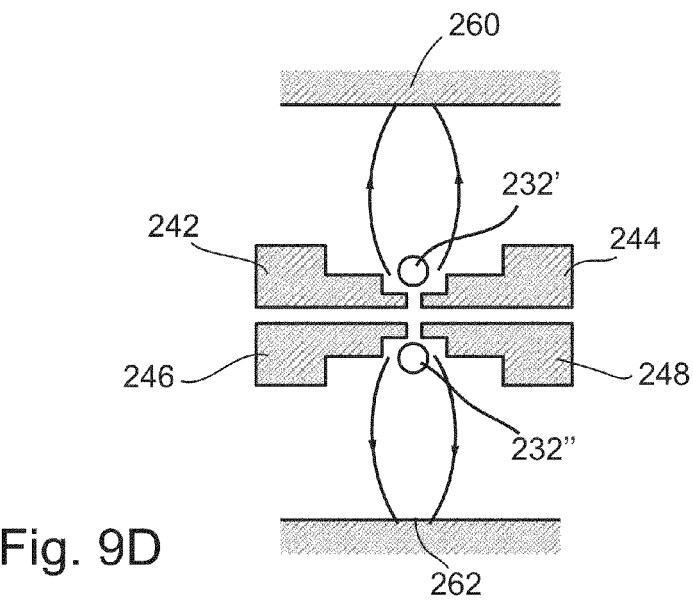
FIG. 9D is a cross-sectional view of the cathode assembly of FIG. 9C.

This construction facilitates the placement of electrodes (not shown) for producing a more focused beam to impinge on target areas 260 and 262 and also makes it possible to position the filaments 232' and 232" parallel to X-ray emitting surfaces of anodes 260 and 262, respectively (not shown). FIG. 9D is a cross-sectional view of the cathode assembly of FIG. 9C.

Figure 9E:
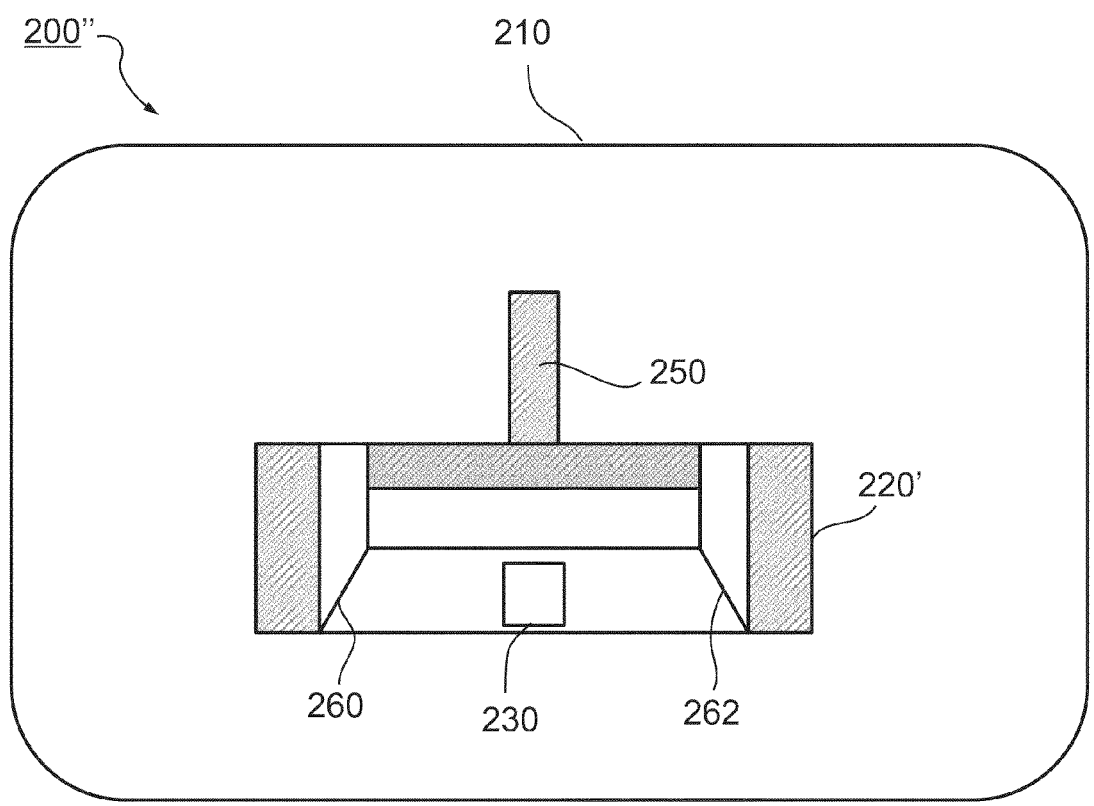
FIG. 9E schematically depicts relevant portions of a third exemplary X-ray tube according to an embodiment of the invention.

FIG. 9E shows an alternative construction of the anode portion of an X-ray tube 200" on a partly cross-sectional view, in accordance with an embodiment of the invention. In this embodiment, a single anode structure 220' rotated around a shaft 250' contains both targets 260 and 262. This construction is simpler. However, since both beams impinge on the same anode structure, the total heat capacity (and the maximum power output) is reduced considerably. The cathode assembly of either FIG. 9A/B or 9C/D can be used with this embodiment. Cathode assembly 230 is shown as a box, to indicate that the constructions of either FIG. 9A/B or FIG. 9C/D can be used.

Although rotating anodes are generally needed for CT, as indicated above, the present invention is also usable for other applications, in which case stationary anode structures can be used.

Figure 10A:
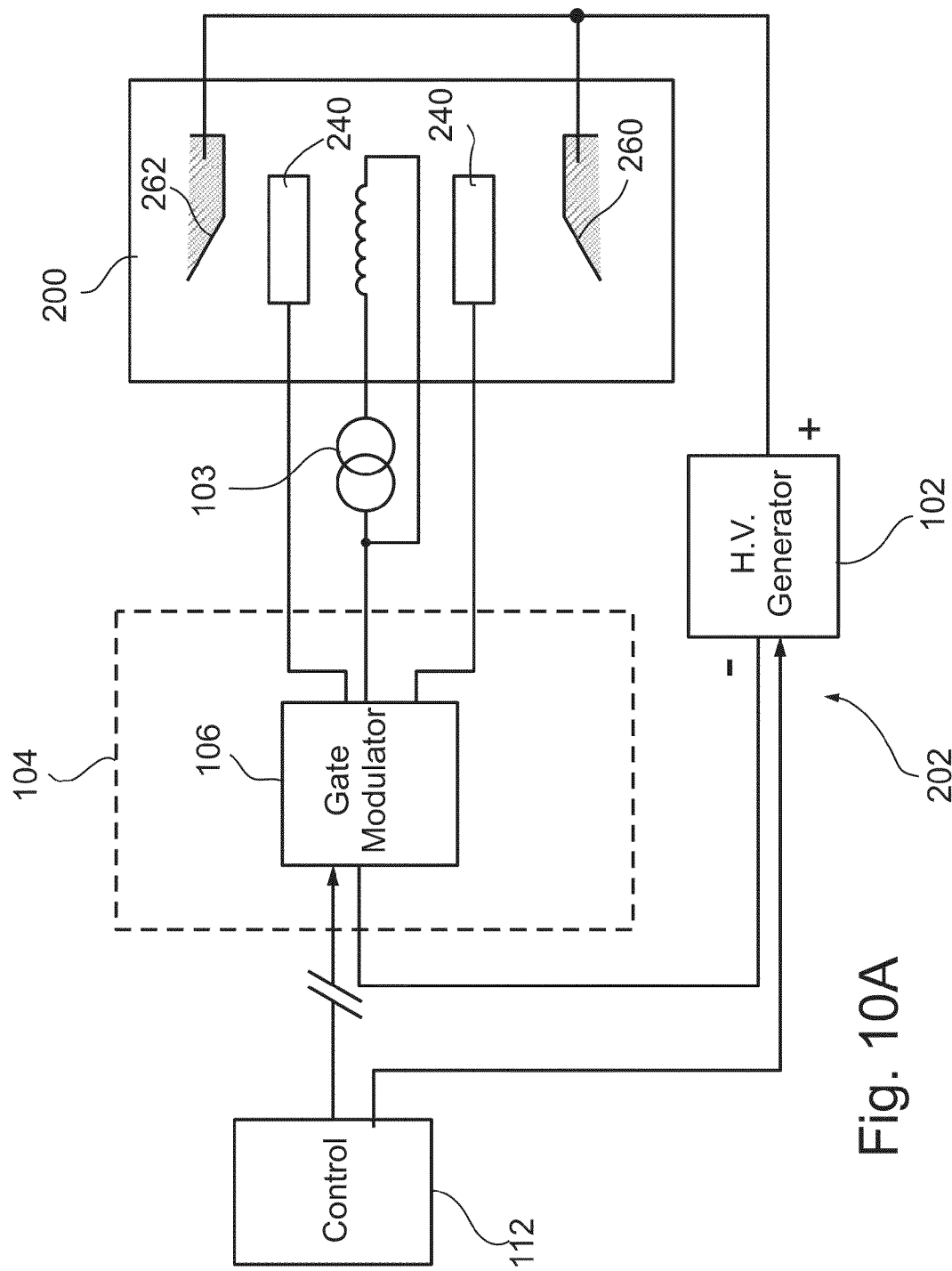
FIG. 10A is a schematic representation of control circuitry adapted for alternately producing an X-ray beam from at least two anodes in a single X-ray tube which are powered with a single high voltage source in accordance with some embodiments of the present invention.

FIG. 10A shows a simplified block diagram of an exemplary system 202 for energizing the X-ray tubes of FIGS. 9A-E where both elements of each gate are at the same potential. The block diagram shown in FIG. 10A represents just one way to energize the tube. In general, any methodology which allows for the application of a high voltage between the anode and cathode and which allows for switching the voltages between cathode and gate between blocking and transmitting voltages for an electron beam can be used.

System 202 comprises a high voltage part 102, a filament current part 103, a gate voltage part 104 and a control 112.

In most systems high voltage part 102 comprises a high voltage power supply connected between the cathode(s) and anode(s). As indicated above the anode or cathode (or neither) can be grounded. For this reason no grounding is shown in FIG. 10A Filament current part 103 is a current power supply generating the current needed to heat the filament in order to induce thermal electron emission.

In the embodiment shown gate voltage part comprises a gate modulator that generates two square wave modulated output voltages, each connected to one of gates 240. In a preferred embodiment the gate modulator output voltages are controllable in the range 0 to −5000 V respective of the filament and modulate at a high frequency in a square wave form between a low and high levels selectable for each gate (see FIG. 11A). The gate voltage levels are selected such that the highly negative level is sufficient to block the flow of electrons from cathode to anode and cut off the X-rays. The less negative level may be 0 or a value sufficient to focus the electron beam to a desired size but yet to transmit the electron beam. A gate modulator has two states. In a first state the cut off voltage is applied to a first gate 240 and the transmit voltage is applied to a second gate 240. In a second state, the cut off voltage is applied to second gate 240 and the transmit voltage is applied to first gate 240. Thus, in the first state an electron beam impinges a second target 262 (associated with gate second gate 240) and there is no beam a first target 260. In the second state an electron beam impinges the first target and not the second target. This results in a controllable excitation of the first and second targets to produce X-rays in alternation.

Figure 10B:
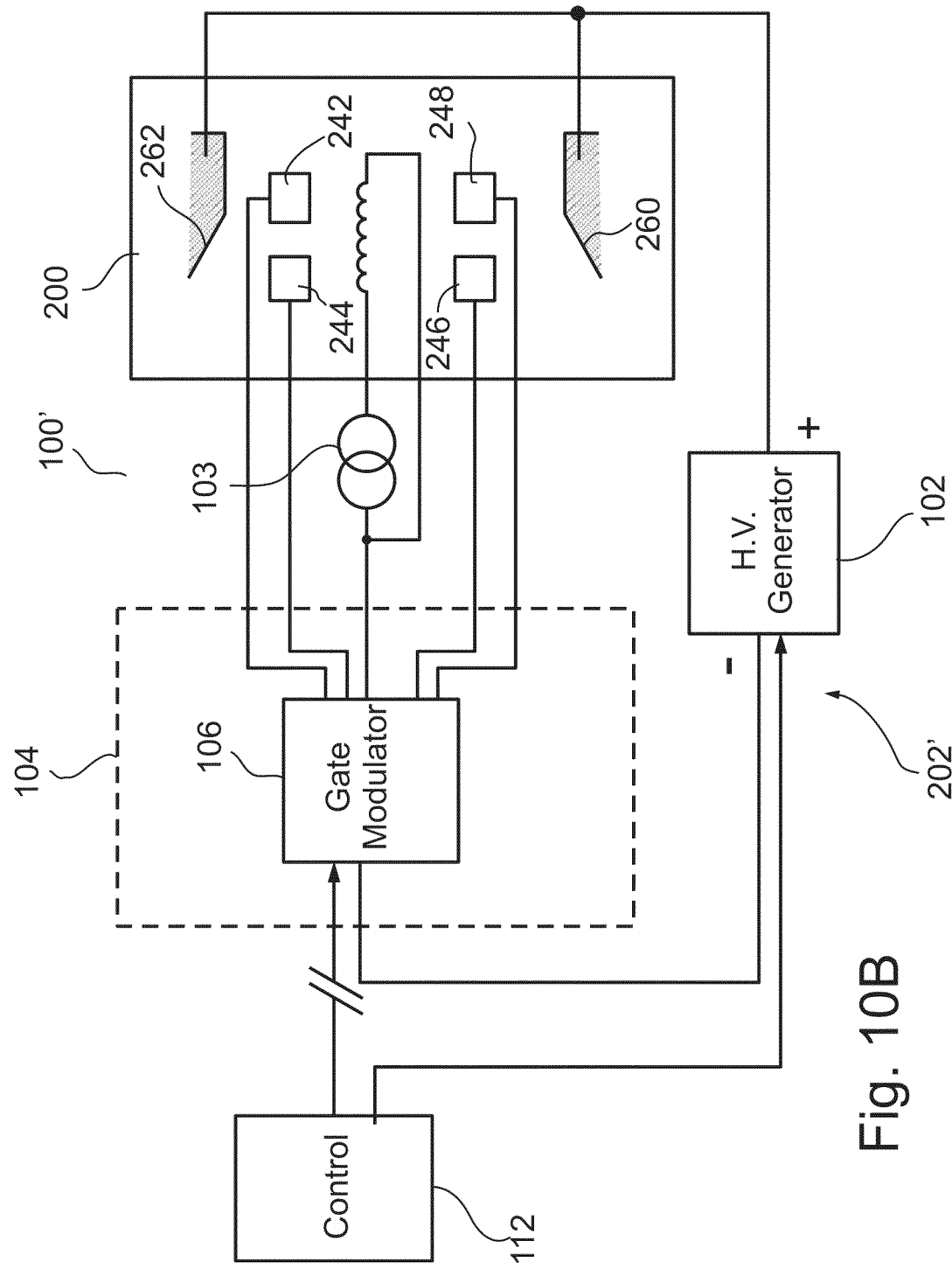
FIG. 10B is a schematic representation of control circuitry adapted for alternately producing an X-ray beam from at least two anodes in a single X-ray tube which are powered with a single high voltage source in accordance with some embodiments of the present invention and in addition deflecting the beam slightly so that the tube can emit beams from four targets.

FIG. 10B is a block diagram of an exemplary circuit 202' for electrifying a tube in which the gate electrodes for each gate are separate and isolated from each other. Cut-off is determined by strongly biasing both electrodes of a set. When the electrodes are differentially electrified, and the beam is not cut off, the difference results in steering of the beam at an angle toward the electrode with the more positive voltage. This results in the beam impinging on the anode at a target point that is slightly displaced along the circumference of the anode. The result is the possibility of generating sets of X-ray sources each set of which is generated by the electrodes in a particular gate and displaced in a first direction by a displacement typically of 5-15 cm. Within the set, the positions of the target/sources can be varied in a direction perpendicular to the first direction by applying differential voltages to the two elements of the gate. The center of focal spot position may typically be steered by 1 mm or more or less.

It is noted that one advantage of the design in FIG. 10A-10B compared to conventional prior art design with a separate HV generator for each source is the reduced cost and simplified design of the system. Another advantage of the design related to the response of the HV power source to fast changes in the load is described below in reference to FIG. 12.

As shown in FIGS. 9B and 9D, electrodes 242, 244, 246 and 248 have a triple function, namely to gate the beam on and off, to focus the beam and to steer the beam. As is known in the art, these functions can be divided among different electrodes 290 and grids (not shown), and the present invention includes such variations. As shown the circuitry shown in FIG. 10B is capable of generating independent voltages for each of the four electrodes.

In an embodiment of the invention control 112 controls gate modulator 106 and optionally HV Generator 102. Control may also have an output which transmits the current state of circuit 202' to a data acquisition system or a computer which receives signals corresponding to attenuation of the X-rays generated by tube 200.

In a fast CT scanner rotation time of the gantry may be of the order of 250 to 500 ms. Generally, to acquire a full set of views using a cone beam, rotation of 180°+ twice the cone angle is required. In order to acquire 1000 views per rotation for each of two focal spots, the required switching frequency is 2 to 4 kHz. For generating multiple beams in each set, a higher modulation rate would be required. In practice, depending on the rotation rate and other factors, the modulation frequency could be between 1-4 kHz, or even between 500 Hz and 8 kHz For use in angiography applications the frequency may be 25/30 or 50/60 Hz or a higher or lower value.

Optionally, a low negative transmit voltage, such as −1.0 or −2.0 kV is applied to open gates 240 depending on the geometry of the cathode, anode and gate. In an exemplary embodiment of the invention, application of a low negative voltage to an open gate 240 focuses the electron beam and/or controls a focal spot dimension. Optionally the cut-off voltage for a tube operating at 120 kV is in the range −4000 or −5000 volts.

Figure 11A:
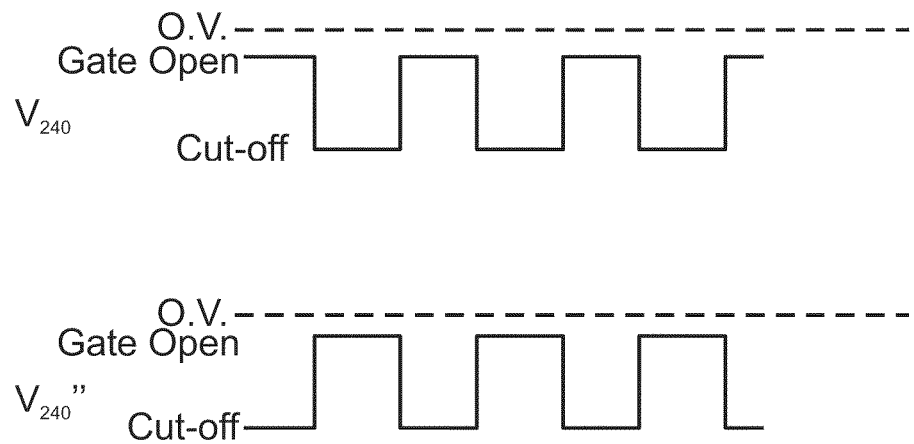
FIGS. 11A and 11B schematically show voltage wave forms for the energizing X-ray tubes using the circuits of FIGS. 10A and 10B respectively.
Figure 11B:
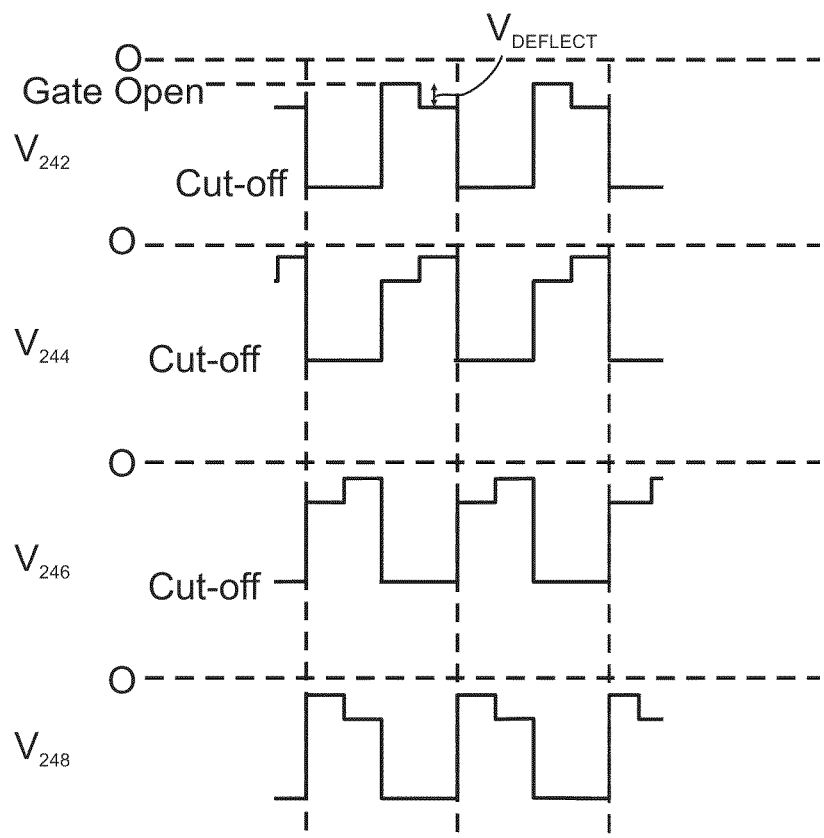

FIGS. 11A and 11B shows switching voltages for the circuits of FIGS. 10A and 10B respectively. In FIG. 11B, voltages are provided for two source positions of X-ray on each anode, with the focal spot being modulated between the four positions each cycle. Beam deflection is not limited to discrete focal spots (square wave). Sine wave deflection or other is possible as well.

Note that while the electrodes shown can be used to deflect the beam in only one direction. It is possible to deflect the beams in the second direction (up-down in FIGS. 9A, 9C and 9E) by means known in the art, such as for example, a pair of deflecting plates situated between the cathode and anode. Alternatively, the beam may be deflected using a varying magnetic field. Alternatively or additionally, the primary deflection, described above using two electrodes, can be performed using either plate electrodes or magnetic fields.

Figure 12:
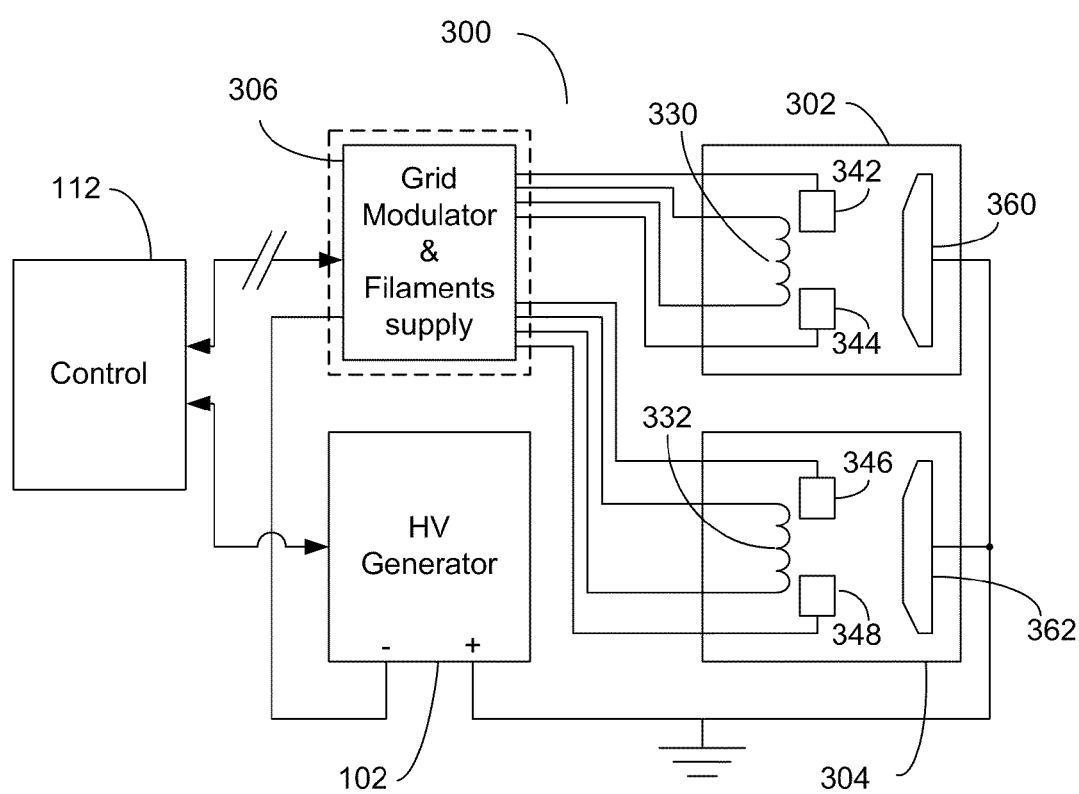
FIG. 12 is a schematic block diagram of an a control unit and power generator for alternately producing an X-ray beam from at least two X-ray tubes which are powered with a single high voltage source in accordance with some embodiments of the present invention.

FIG. 12 is a schematic block diagram of an a control unit and power generator for alternately producing an X-ray beam from at least two X-ray tubes which are powered with a single high voltage source in accordance with some embodiments of the present invention. According to some embodiments of the present invention, X-ray system 300 includes two X-ray tubes 302 and 304 controlled by control circuit 112 and energized by a single High Voltage (HV) generator 102. In some exemplary embodiments, HV generator 102 provides voltage levels between 80 KV and 140 KV. Optionally, the anodes voltage (positive output of generator 102) may be grounded, as shown in FIG. 12, or optionally the cathodes may be grounded or optionally both anodes and cathodes are at a voltage relative to ground. Typically, X-ray tubes 302 and 304 include filaments 330 and 332, grid electrodes 342, 344, 346, and 348, and anodes 360 and 362 respectively. Other parts of the tubes are not shown for simplicity. According to some embodiments of the present invention, grid modulator and filament supply unit 306 applies alternating voltage to grid electrodes 342, 344, 346, and 348 and provides heating current to the filaments 330 and 332. Optionally, system 300 is operated in a similar manner to systems 200, 200' and 200" described above in relation to FIG. 9A-9E. X-ray tubes 302 and 304 may for example be operated with each pair of electrodes in a tube biased at the same voltage as described by FIG. 11A or with different voltage to each gate electrode as described by FIG. 11B. Typically, each of X-ray tubes 302 and 304 is operated in a pulsed mode with duty cycle of 50% or less. Optionally the pulsed grid voltages range between 0 and −5 KV. Optionally the grid modulator applies grid voltages for blocking the filament electron beam during one part of its cycle and grid voltages for focusing and/or steering the filament electron beam during another part of its cycle. It is noted that X-ray sources described in reference to FIGS. 10A and 10B may similarly be operated in a pulsed mode with duty cycle of 50% or less.

According to some embodiments of the present invention, a common feature of embodiments described in connection to FIGS. 10A-10B and 12 is the operation of two X-ray sources wherein each source is pulsed at high frequency, e.g. between 0.5 KHz to 10 KHz. Optionally, pulse duration is between 50 μsec and 1 msec but higher or lower values may be used. It is noted that although pulsed X-ray sources are well known in the art, the pulsing rate is typically low, e.g. up to 60 pulses per second and pulse duration is typically 5 msec or more. Known pulse system include for example X-ray fluoroscopy and angiography system that acquire multiple X-ray images per second. For such systems the HV rise-time and fall-time typically desired are in the range of 1 msec. Such rise and fall times are typically attainable. According to some embodiments of the present invention, high frequency high voltage switching is achieved by using grid modulator and filament supply unit 306. One of ordinary skill in the art will recognize that high frequency high voltage switching by grids does not suffer from rise-time and fall-time limitations but suffers from voltage transients and/or oscillations during switching because of the sudden changes in load on the generator.

The present inventor has found, that circuitry such as described in connection with FIGS. 10A, 10B and 12 avoid transients due to changes of load on the generator. Specifically with regard to the system shown in FIG. 12, according to some embodiments of the present invention, a single high voltage source 102 applies high voltage continuously between filaments 330 and 332 and anodes 360 and 362, respectively. In some exemplary embodiments of the present invention, X-ray sources 302 and 304 are designed and operated such that they present substantially same load to the generator. Thus, the generator may be operated with substantially constant load and constant voltage level while switching between X-ray tubes and transients can be avoided. Optionally, generator 102, modulator 106 and source 200 in FIGS. 10A and 10B are similarly operated. Typically, controller 112 and grid modulator 306 are operative to apply blocking voltages on the electrodes of one source at a time, as described in FIG. 11A or 11B. According to some embodiments of the present invention, the timing of the grid voltages modulations are adjusted such that at any one time one source and only one source is loading the generator. Optionally, the switching time from one source to the other is shorter than 10 μsec or shorter than 5 μsec or shorter than 1 μsec.

In an exemplary embodiment of the invention, where the tube or tubes are used in a cone beam CT scanner, a distance between the focal spots and the axis of rotation (SAD) is 500 mm. This optional configuration provides coverage of 140 mm at isocenter. In general in wide angle cone beam CT a cone opening in the Z direction (for each X-ray beam) is ±6-15°. In an exemplary embodiment of the invention, the anode angle should be at least 8-18° to avoid a heel effect under these conditions. In some uses of the present invention (such as, for example that shown above, where the beam is asymmetric (with a greater angle toward the cathode), the anode angle can be considerably smaller. In other embodiments, both beams are symmetrical. In the embodiment of FIG. 5, the beam of the central source is symmetrical. In an exemplary embodiment of the invention, a short exposure time is used for imaging of a rapidly moving tissue (e.g. cardiac tissue). Optionally, an increase in a power rating of X-ray tube 200 contributes to an ability to achieve an acceptable image contrast with a short exposure time. In an exemplary embodiment of the invention, use of alternating anodes 220 as described above in FIGS. 9A and 9C, contributes to a reduction in anode heating. Optionally, the reduction in anode heating contributes to a feasibility of using a tube with a higher power rating. In the embodiment depicted in FIGS. 9A and 9C, heat load on each of anodes 220 are 50% of comparable loads in a conventional single anode X-ray tube.

One of ordinary skill in the art will be able to select and configure other portions of X-ray tubes 200, 302 or 304 and/or control circuitry 112 such as a housing and/or anodes and/or filaments and/or gate electrodes and/or HV generator 102 and/or cabling and/or high voltage connectors from commercially available components. For clarity, these portions of X-ray tubes 200, 302 and 304 and/or control circuitry 112 are not shown and/or represented only schematically. For example X-ray tubes are described as having thermal filament in the cathode. However other types of cathodes may be used, in which case the grid electrode structure and voltages may be configured for the other type of cathodes.

A variety of numerical indicators have been utilized to describe various components of the X-ray tube and/or voltages and/or power inputs. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as sub-units may be combined into a single unit with the described/depicted function.

It should be further understood that the individual features described hereinabove can be combined in all possible combinations and sub-combinations to produce exemplary embodiments of the invention. The examples given above are exemplary in nature and are not intended to limit the scope of the invention which is defined solely by the following claims. Specifically, the invention has been described in the context of a left atrium but might also be used in a right atrium or a ventricle.

As used in the description and claims of the present invention, the term "cone beam" means a beam having a cone angle (in the direction of the axis of the scanner) or at least two degrees.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively and additionally, portions of the invention described/depicted as a single unit may reside in two or more separate physical entities which act in concert to perform the described/depicted function. Alternatively and additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

All publications and/or patents and/or product descriptions cited in this document are fully incorporated herein by reference to the same extent as if each had been individually incorporated herein by reference.

I claim:

1. Apparatus for CT cone beam scanning, comprising:
a table for holding a subject;
a gantry defining a rotation axis of the apparatus;
a first detector array, mounted on the gantry;
an X-ray source system comprising:
a plurality of X-ray sources, wherein each X-ray source of the plurality is provided with a cathode from which an electron beam is emitted, an anode to receive the electron beam and at least one grid electrode, wherein the grid electrodes are configured to selectively block radiation from the plurality of X-ray sources;
a high voltage generator for applying voltage to the plurality of X-ray sources;
a grid modulator configured to apply voltage to grid electrodes of each of the plurality of X-ray sources in turn;
a controller for controlling the grid modulator so that only one of the plurality of X-ray sources emits a cone beam at any one time; and
a collimator that collimates cone beams from two of the plurality of X-ray sources such that the cone beams are asymmetrical with respect to a plane defined by each respective X-ray source trajectory about the rotation axis, and an edge of at least one asymmetrical cone beam which is farther from the other X-ray source makes a larger angle to the detector array than does the beam edge closer to the other X-ray source; and such that the farther edge of the at least one asymmetrical cone beam makes an angle of between 87 and 90 degrees with the detector array; and
a scanning controller that acquires data responsive to radiation from the plurality of X-ray sources from the detector array, wherein the radiation acquired is attenuated by at least part of a common volume of a subject irradiated by the plurality of X-ray sources.

2. The apparatus according to claim 1, wherein the grid modulator is configured to alternately provide a pulsed voltage to at least one of the plurality of X-ray sources for blocking the radiation, the pulsed voltage pulsed at a frequency between 0.5 KHz to 10 KHz.

3. The apparatus according to claim 2, wherein the grid modulator is configured to provide a pulsed voltage for blocking the radiation with a duty cycle of 50% or more.

4. The apparatus of claim 1, wherein the grid modulator is configured to apply a same voltage to a plurality of grid electrodes associated with any one of the plurality of X-ray sources.

5. The apparatus of claim 1, wherein the grid modulator is configured to apply a different voltage to each of a plurality of grid electrodes associated with any one of the plurality of X-ray sources.

6. The apparatus of claim 1, wherein the grid modulator applies voltages between 0 and −5 KV to the grid electrodes.

7. The apparatus of claim 1, wherein the plurality of X-ray sources includes two X-ray tubes.

8. The apparatus of claim 1, wherein the grid modulator is additionally configured for modulating the voltage for focal spot position modulation.

9. The apparatus of claim 1, wherein an X-ray source of the plurality is provided with at least one pair of grid electrodes and wherein the at least one pair of grid electrodes is configured to focus the electron beam to reduce a size of a focal spot on an anode.

10. The apparatus of claim 1, wherein the voltage is applied to the at least one grid electrode of an X-ray source over a period of time, and wherein the grid modulator is configured to apply the voltages for blocking radiation from the X-ray source during one part of the period and to apply the voltage for steering or focusing the electron beam of the X-ray source during another part of the period.

11. The apparatus according to claim 10, wherein the voltages applied to the at least one grid electrode is a pulsed voltages.

12. The apparatus of claim 1, wherein the detector array has a given number of rows of detector elements spaced along a rotation axis of the gantry.

13. The apparatus of claim 12, wherein the number of rows is at least twice the number of sources.

14. The apparatus according to claim 1 and further comprising:
a second detector array, having a given number of rows of detector elements spaced along an rotation axis of the gantry, mounted on the gantry;
a second plurality of X-ray sources mounted on the gantry for rotation about the patient table on the rotation axis, the number of rows being at least twice the number of sources; and
wherein the scanning controller acquires data responsive to radiation from the first and second plurality of sources from both the first and second detector arrays attenuated by at least part of the common volume of the subject irradiated by the first and second plurality of radiation sources.

15. The apparatus according to claim 14 wherein the second detector array and the second plurality of X-ray sources are circumferentially offset from the first detector array and first plurality of X-ray sources.

16. The apparatus of claim 1 comprising a single high voltage generator for applying voltage to the plurality of X-ray sources, wherein each of the plurality of X-ray sources is configured to present substantially the same load to the high voltage generator.

17. The apparatus according to claim 16, wherein the high voltage generator supplies a continuous voltage during switching between each of the plurality of X-ray sources.

18. The apparatus of claim 16, wherein the high voltage generator generates voltages between 80 KV to 140 KV.

19. A method for activating a plurality of X-ray sources for CT scanning, the method comprising:
providing a plurality of X-ray sources each including at least one grid electrode;
applying voltage to each of the plurality of X-ray sources with a high voltage generator; and
collimating the cone beams from two of the plurality of X-ray sources such that the cone beams are asymmetrical with respect to a plane defined by each respective source trajectory about a rotation axis of a CT scanner, and an edge of at least one asymmetrical cone beam which is farther from the other X-ray source makes a larger angle to the detector array than does the beam edge closer to the other source; and such that the farther edge of the at least one asymmetrical cone beam makes an angle of between 87 and 90 degrees with the detector array; and
enabling radiation from one of the plurality of X-sources at a time and blocking radiation from the other X-ray sources of the plurality with the grid of electrodes so that only one of the plurality of X-ray sources emits a cone beam at any one time.

20. The method according to claim 19, wherein the voltage applied to said grid electrodes is a pulsed voltage that is pulsed at a frequency between 0.5 KHz to 10 KHz.

21. The method according to claim 20, wherein the pulse voltage has a duty cycle of 50% or more.

22. The method of claim 19, wherein a same voltage is applied to each of the grid electrodes associated with any one of the plurality of X-ray sources.

23. The method of claim 19, wherein the grid voltage applied to said grid electrodes is between 0 and −5 KV.

24. The method of claim 19, wherein the plurality of X-ray sources includes two X-ray tubes.

25. The method of claim 19, wherein the plurality of X-ray sources includes a plurality of X-ray sources in a single vacuum enclosure.

26. The method of claim 19 comprising applying voltage to each of the plurality of X ray sources with a single high voltage generator, wherein each of the plurality of X-ray sources apply substantially the same load to the high voltage generator.

27. The method according to claim 26, wherein the high voltage applied to said plurality of X-ray sources by said HV generator is a continuous voltage.

28. The method of claim 26, wherein the high voltage generator generates voltages between 80 KV to 140 KV.

* * * * *